US010908053B2

(12) United States Patent
Smith

(10) Patent No.: US 10,908,053 B2
(45) Date of Patent: Feb. 2, 2021

(54) DISTILLATION PROBES AND METHODS FOR SAMPLING AND CONDITIONING A FLUID

(71) Applicant: Smith Analytical, LLC, Seabrook, TX (US)

(72) Inventor: Stevie Horton Smith, Seabrook, TX (US)

(73) Assignee: SMITH ANALYTICAL, LLC, Seabrook, TX (US)

( * ) Notice: Subject to any disclaimer, the term of this patent is extended or adjusted under 35 U.S.C. 154(b) by 233 days.

(21) Appl. No.: 15/933,353

(22) Filed: Mar. 22, 2018

(65) Prior Publication Data

US 2018/0275024 A1 Sep. 27, 2018

Related U.S. Application Data

(60) Provisional application No. 62/474,977, filed on Mar. 22, 2017.

(51) Int. Cl.
*G01N 1/22* (2006.01)
*B01D 53/00* (2006.01)
(Continued)

(52) U.S. Cl.
CPC ........... *G01N 1/2247* (2013.01); *B01D 45/08* (2013.01); *B01D 53/002* (2013.01); *B01D 53/30* (2013.01); *C07C 4/02* (2013.01); *G01N 1/2035* (2013.01); *G01N 1/2202* (2013.01); *B01D 2257/70* (2013.01); *B01D 2257/80* (2013.01); *G01N 2001/2267* (2013.01); *G01N 2001/2282* (2013.01)

(58) Field of Classification Search
CPC .. G01N 1/2247; G01N 1/2035; G01N 1/2202; B01D 45/08
See application file for complete search history.

(56) References Cited

U.S. PATENT DOCUMENTS 2,202,800 A   5/1940   Kiewig
2,398,836 A   4/1946   Lea
(Continued)

FOREIGN PATENT DOCUMENTS

JP      S5815002 B2    3/1983
WO    2011/097122 A2   8/2011

OTHER PUBLICATIONS

PCT/US2011/022824 International Search Report and Written Opinion dated Sep. 29, 2011 (10 p.).
(Continued)

*Primary Examiner* — David Z Huang
(74) *Attorney, Agent, or Firm* — Conley Rose, P.C.

(57) ABSTRACT

A distillation probe includes a conduit having a central axis. In addition, the distillation probe includes a baffle assembly disposed in the conduit. The baffle assembly includes a plurality of axially-spaced baffles positioned one-above-the-other in a stack within the conduit. Further, the distillation probe includes a first helical cooling coil wrapped around the conduit. Moreover, the distillation probe includes a thermally conductive layer disposed about the conduit and encapsulating the first helical cooling coil. The thermally conductive layer is configured to transfer thermal energy between the first helical cooling coil and the conduit.

26 Claims, 13 Drawing Sheets

(51) Int. Cl.
 B01D 53/30 (2006.01)
 C07C 4/02 (2006.01)
 B01D 45/08 (2006.01)
 G01N 1/20 (2006.01)

(56) References Cited

U.S. PATENT DOCUMENTS

| | | | |
|---|---|---|---|
| 3,135,684 A | 6/1964 | Jakob et al. | |
| 3,811,252 A * | 5/1974 | Evans | B01D 45/08 |
| | | | 96/237 |
| 4,461,183 A | 7/1984 | Wedding | |
| 4,642,043 A * | 2/1987 | Schwarzkopf | B29C 45/2737 |
| | | | 264/328.15 |
| 5,229,014 A | 7/1993 | Collins | |
| 5,837,203 A | 11/1998 | Godec et al. | |
| 5,884,414 A | 3/1999 | Anger | |
| 6,205,869 B1 | 3/2001 | Schadt et al. | |
| 6,436,245 B1 | 8/2002 | Nishimura et al. | |
| 6,530,979 B2 | 3/2003 | Firey | |
| 6,666,905 B2 | 12/2003 | Page et al. | |
| 6,713,112 B1 | 3/2004 | Lucas | |
| 6,761,757 B2 | 7/2004 | Welker | |
| 7,032,444 B2 | 4/2006 | Breviere et al. | |
| 7,081,146 B2 | 7/2006 | Hallgren et al. | |
| 7,250,066 B2 | 7/2007 | Seipler | |
| 7,513,940 B2 | 4/2009 | Mileham | |
| 7,569,094 B2 | 8/2009 | Kane et al. | |
| 7,833,303 B1 | 11/2010 | Higgins | |
| 7,927,395 B2 | 4/2011 | Szepessy et al. | |
| 7,993,425 B2 | 8/2011 | Corattiyil et al. | |
| 8,211,210 B2 | 7/2012 | Smith | |
| 9,188,517 B2 * | 11/2015 | Smith | G01N 1/2247 |
| 2003/0044331 A1 | 3/2003 | DeBellis et al. | |
| 2003/0233890 A1 | 12/2003 | Mayeaux | |
| 2004/0079236 A1 | 4/2004 | Welker | |
| 2005/0087028 A1 | 4/2005 | Widmer | |
| 2005/0198932 A1 | 9/2005 | Franzen et al. | |
| 2006/0037853 A1 | 2/2006 | Roan et al. | |
| 2008/0017040 A1 | 1/2008 | Mileham et al. | |
| 2009/0266235 A1 | 10/2009 | Kane et al. | |
| 2010/0180854 A1 | 7/2010 | Baumann et al. | |
| 2013/0061969 A1 * | 3/2013 | Koike | H01L 21/67017 |
| | | | 138/37 |
| 2014/0262741 A1 | 9/2014 | Bowers et al. | |

OTHER PUBLICATIONS

PCT/US2018/023897 International Search Report and Written Opinion dated Jul. 16, 2018 (19 p.).
Search Report for European Application No. 18770608.0 dated Sep. 15, 2020 (8 p.).

* cited by examiner

DISTILLATION PROBES AND METHODS FOR SAMPLING AND CONDITIONING A FLUID

CROSS-REFERENCE TO RELATED APPLICATIONS

This application claims benefit of U.S. provisional patent application Ser. No. 62/474,977 filed Mar. 22, 2017, and entitled "Distillation Probes and Methods for Sampling and Conditioning a Fluid," which is hereby incorporated herein by reference in its entirety.

STATEMENT REGARDING FEDERALLY SPONSORED RESEARCH OR DEVELOPMENT

Not applicable.

BACKGROUND

The invention relates generally to systems and methods for analyzing fluid samples. More particularly, the invention relates to systems and methods for separating liquids from gases in a hydrocarbon fluid sample streams to condition the gases for subsequent analyses.

In refineries and chemical plants, analytical instrumentation is employed at different stages to analyze the composition of the various fluids being processed. In most cases, a small sample of fluid is taken from a process stream and routed to the instrumentation that performs the analysis. Depending on the type of instrumentation and analysis, the fluid sample may need to be "conditioned" before entering the instrumentation to remove liquids or contaminants that may otherwise harm the instrumentation or negatively influence the analytical results (e.g., skew the analytical results such as product yield results).

BRIEF SUMMARY OF THE DISCLOSURE

Embodiments of distillation probes are disclosed herein. In one embodiment, a distillation probe comprises a conduit having a central axis. In addition, the distillation probe comprises a baffle assembly disposed in the conduit. The baffle assembly includes a plurality of axially-spaced baffles positioned one-above-the-other in a stack within the conduit. Further, the distillation probe comprises a first helical cooling coil wrapped around the conduit. Still further, the distillation probe comprises a thermally conductive layer disposed about the conduit and encapsulating the first helical cooling coil. The thermally conductive layer is configured to transfer thermal energy between the first helical cooling coil and the conduit.

Embodiments of fluid sampling systems are disclosed herein. In one embodiment, a fluid sampling system comprises a fluid separator assembly. The fluid separator assembly includes a conduit and a baffle assembly disposed in the conduit. The conduit has a central axis. The baffle assembly includes a plurality of axially-spaced baffles positioned one-above-the-other in a stack within the conduit and a flexible cable extending through each of the baffles. In addition, the fluid sampling system comprises a plurality of cooling conduits mounted to the conduit and positioned radially adjacent the conduit. The cooling conduits are configured to cool the fluid separator assembly.

Embodiments described herein comprise a combination of features and advantages intended to address various shortcomings associated with certain prior devices, systems, and methods. The foregoing has outlined rather broadly the features and technical advantages of the invention in order that the detailed description of the invention that follows may be better understood. The various characteristics described above, as well as other features, will be readily apparent to those skilled in the art upon reading the following detailed description, and by referring to the accompanying drawings. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF SOME OF THE PREFERRED EMBODIMENTS

Figure 1:
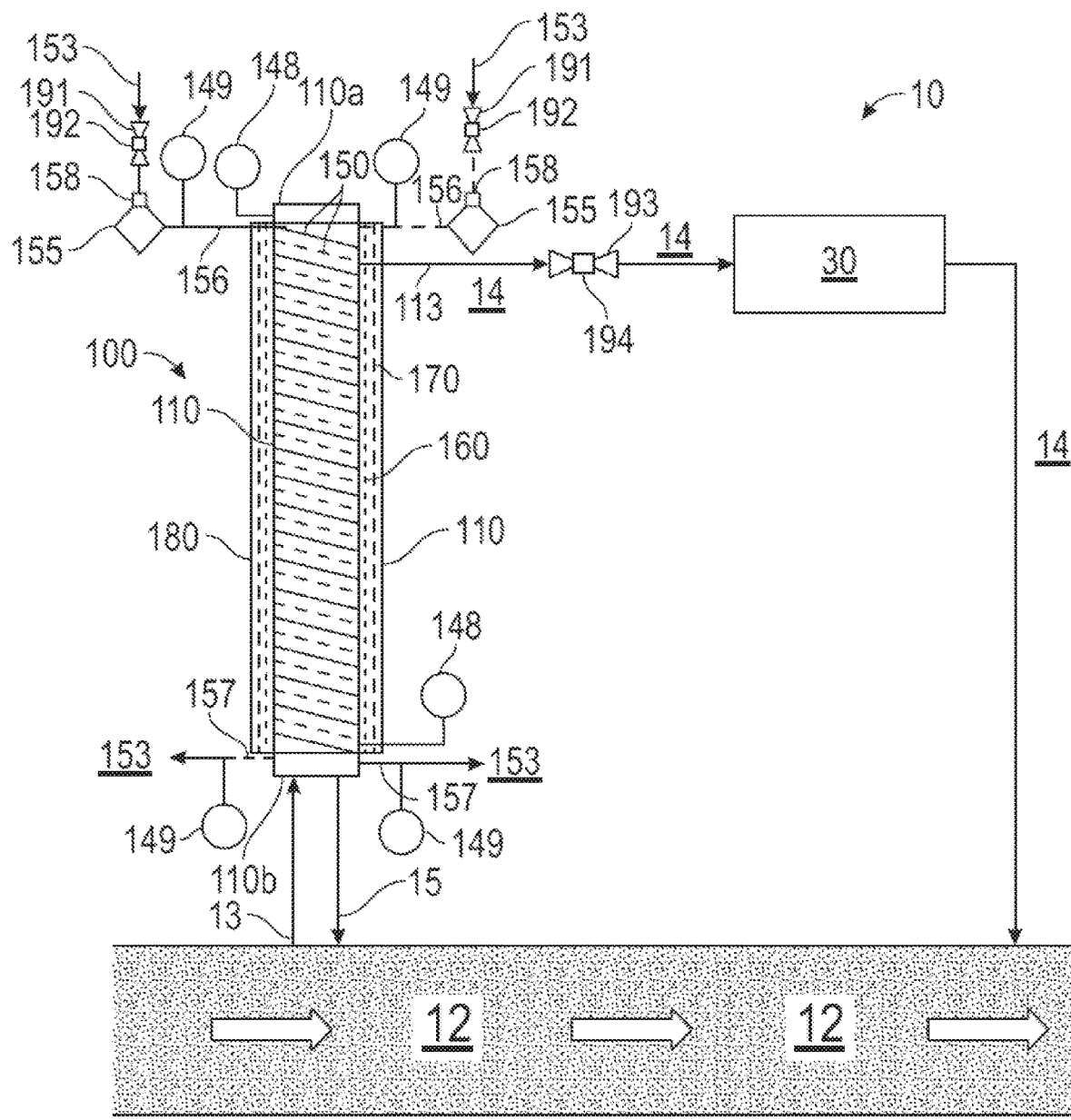
FIG. 1 is a schematic view of an embodiment of a system for sampling a bulk chemical or hydrocarbon fluid stream.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Referring now to FIG. 1, an embodiment of a system 10 for sampling a bulk fluid stream 12 is shown. In general, fluid stream 12 can be any hydrocarbon or chemical fluid stream for which compositional analysis is desired. In this exemplary embodiment, stream 12 is a hydrocarbon fluid stream such as a decoke or green oil fluid stream within a hydrocarbon cracking or pyrolysis operation. System 10 includes a fluid conditioner 100 and analytical instrumentation 30 downstream from conditioner 100. The bulk fluid stream 12 is sampled and analyzed to provide insight into the processing operation. For example, in a hydrocarbon cracking operation, the fluid stream 12 may be a bulk decoke fluid stream that is sampled and analyzed to determine the yield of one or more desired products (e.g., the volume of ethylene or propylene produced by the cracking process per unit time).

System 10 pulls a sample 13 from the fluid stream 12. When sample 13 is initially pulled from the process fluid stream 12, it may contain a mixture of gas 14 to be analyzed and undesirable compounds or contaminants 15 such as water, relatively heavy hydrocarbons (i.e. C6 and heavier), and particulate matter, which can foul and/or damage downstream equipment (e.g., instrumentation 30), negatively impact the accuracy of analytical results produced by instrumentation 30, or combinations thereof. Accordingly, in system 10, sample 13 is routed to and conditioned by fluid conditioner 100 to remove contaminants 15 prior to being directed to analytical instrumentation 30. Thus, conditioner 100 separates sample 13 into contaminants 15, which are fed back to bulk fluid stream 12, and the remaining gas 14, which is passed on to analytical instrumentation 30 for analysis. Analytical instrumentation 30 analyzes gas 14 to determine one or more characteristics of gas 14 (e.g., the composition of gas 14, the yield rate of gas 14, etc.), which is communicated to the plant operators. After analysis, gas 14 is fed from instrumentation back into bulk fluid stream 12. Although only one system 10 and associated conditioner 100 is shown in FIG. 1, it should be appreciated that more than one system 10 and conditioner 100 can be employed in a chemical or hydrocarbon processing operation to sample fluid and condition the sampled fluids at different stages or locations along the processing operations.

As previously described, conditioner 100 can be used in connection with any suitable chemical or hydrocarbon processing operation to separate contaminants 15 and gas 14 prior to analysis with instrumentation 30. In one exemplary embodiment, system 10 is employed to sample and analyze a decoke fluid sample from a hydrocarbon cracking operation to determine the ethylene and/or propylene yields during the cracking operations. In such embodiments, fluid sample 13 is an unconditioned decoke fluid sample comprising contaminants 15 (e.g., water, relatively heavy hydrocarbons (i.e., hydrocarbon molecules having six or more carbon atoms), and small quantities of particulate matter) and gas 14 comprises relatively light hydrocarbons (i.e., hydrocarbons molecules having five or less carbon atoms such as ethylene, propylene, methane, ethane, and propane).

Figure 2:
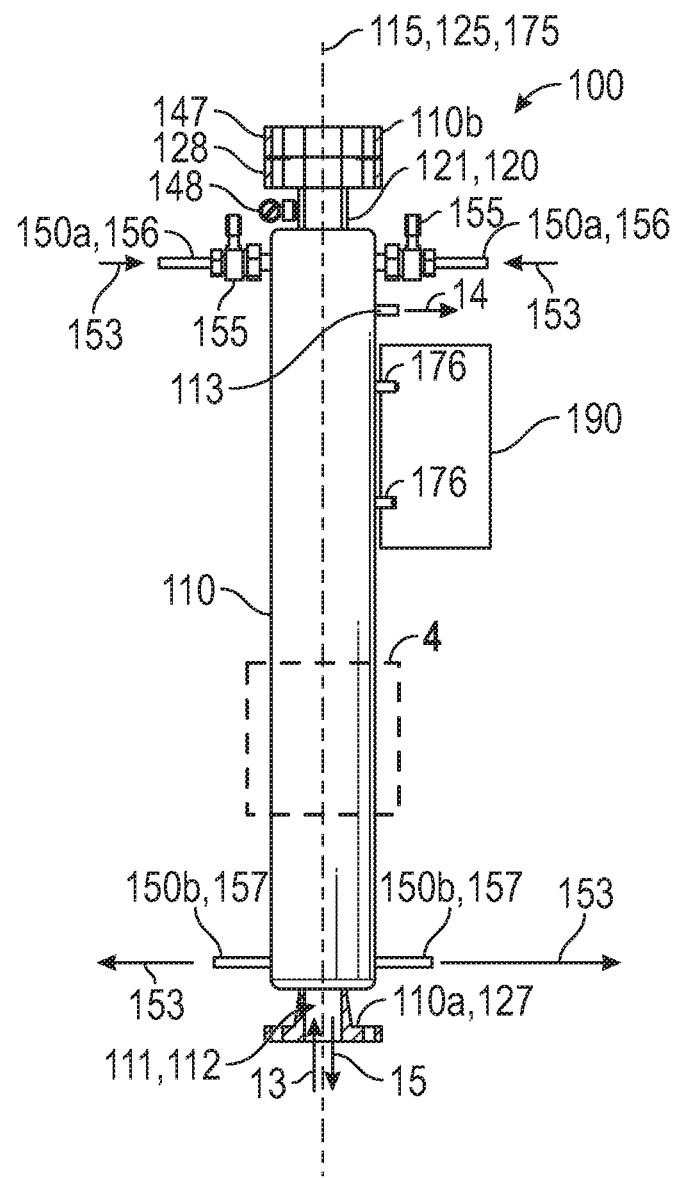
FIG. 2 is a side view of the fluid conditioner of FIG. 1.

Referring now to FIG. 2, fluid conditioner 100 is schematically shown. Conditioner 100 includes a fluid separator 110 and a sample monitoring and control system 190 coupled to separator 110. In FIG. 2, fluid separator 110 is shown in partial cross-sectional view and sample monitoring and control system 190 is schematically shown. The components of system 190 are shown schematically in FIG. 1 and will be described in more detail below.

Fluid separator 110 separates a fluid sample 13 acquired from bulk fluid stream 12 into contaminants 15 and a conditioned gas 14, which is directed to instrumentation 30 for analysis. Accordingly, separator 110 may be described as a fluid conditioner or fluid conditioning device. In addition, as will be described in more detail below, separator 110 utilizes distillation to separate contaminants 15 and gas 14. Namely, during conditioning with separator 110, fluid sample 13 is cooled, and as a result, gaseous contaminants 15 such as water and relatively heavy hydrocarbons phase change to liquid droplets that coalesce within separator 110. Although fluid sample 13 is cooled within separator 110 and gaseous contaminants 15 separate out as liquid, conditioned gas 14 remains a gas, albeit at a lower temperature than fluid sample 13. Thus, separator 110 may also be described as a distillation device or probe.

Sample monitoring and control system 190 measures multiple predetermined parameters associated with the sample separation process and controls the sample separation process within separator 110. For example, system 190 may adjust the sample separating process within separator 110 automatically based on the measured parameters (i.e., without human intervention) and/or in response to input from a remote operator.

Figure 3:
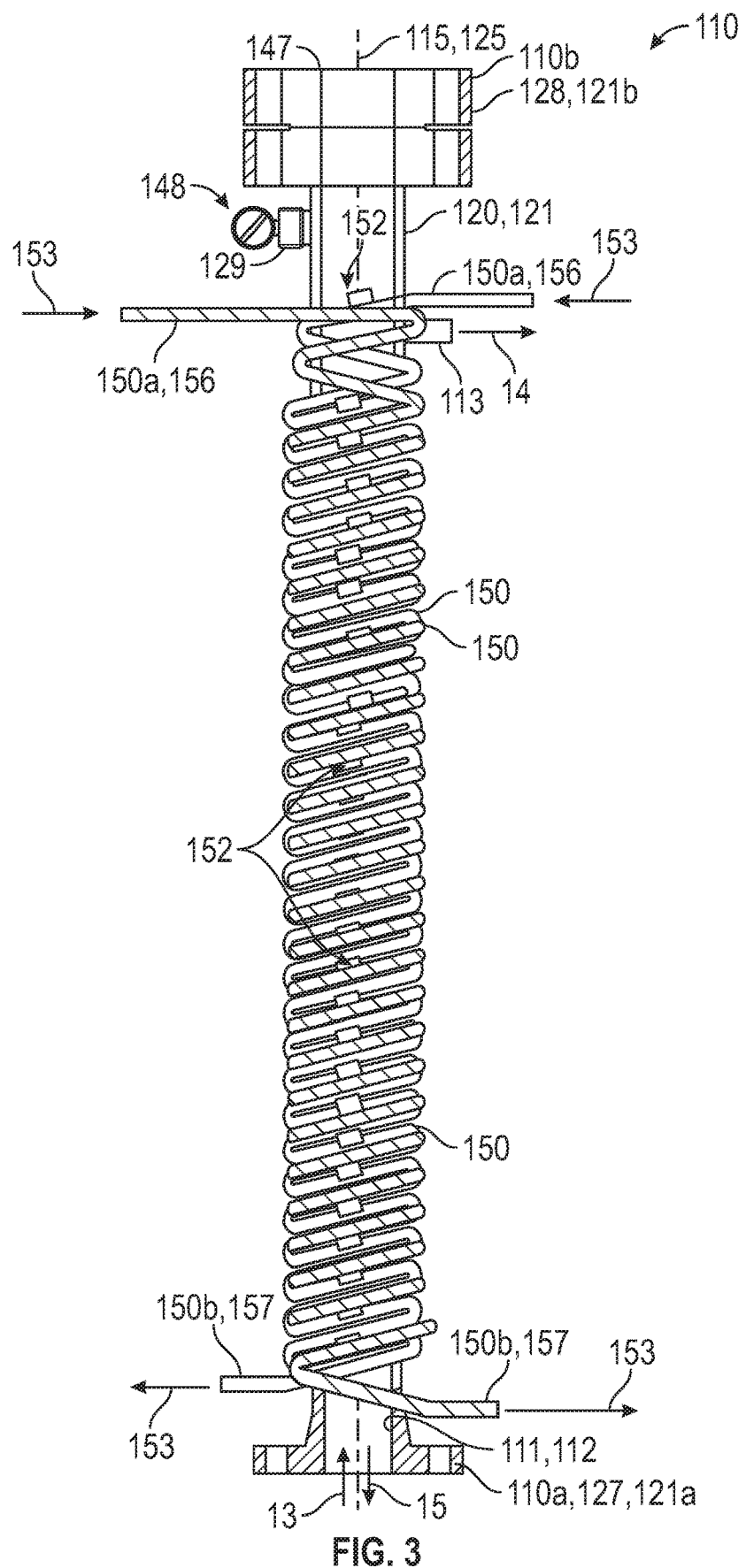
FIG. 3 is a side view of the fluid condition of FIG. 2 without the insulation, protective cover, or thermally conductive layer.
Figure 4:
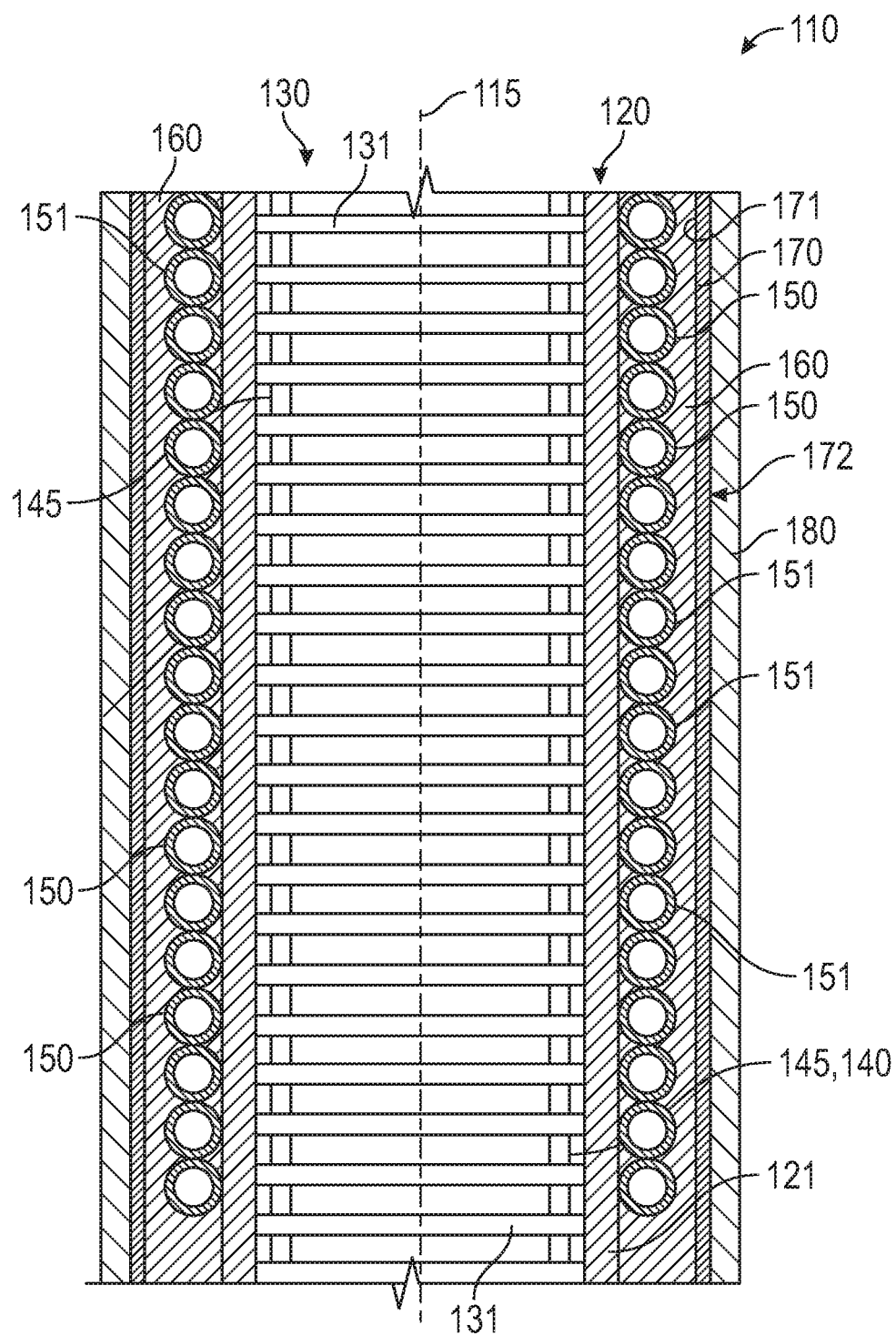
FIG. 4 is an enlarged partial cross-sectional view of the fluid conditioner of FIG. 2 taken in section 4-4 of FIG. 2.

Referring now to FIGS. 2-4, fluid separator 110 has a central or longitudinal axis 115, a first or lower end 110a, and a second or upper end 110b. In this embodiment, separator 110 and its central axis 115 are vertically oriented. As best shown in FIG. 4, moving radially outward from axis 115, fluid separator 110 includes a separator assembly 120, a plurality of tubular cooling conduits 150 disposed about separator assembly 120, a thermally conductive layer 160 disposed about separator assembly 120 and encapsulating conduits 150, a protective tubular cover 170 disposed about layer 160, and insulation 180 disposed about cover 170. Thus, conduits 150 and layer 160 are radially positioned between cover 170 and separator assembly 120, and cover 170 is radially positioned between insulation 180 and layer 160. Cover 170 provides a rigid shield that protects conduits 150 and separator assembly 120 from being impacted and damaged, as well as provides a secure base for mounting system 190 (i.e., system 190 is fixably secured to cover 170. In FIG. 3, layer 160, cover 17, and insulation 180 are not shown to more clearly illustrate separator assembly 120, cooling conduits 150, and the relationship therebetween.

Referring still to FIG. 4, no annular gaps, spaces, or voids are provided between cover 170 and separator assembly 120. In particular, conduits 150 directly engage and contact separator assembly 120, and layer 160 completely surrounds conduits 150 and extends radially between separator assembly 120 and cover 170. Thus, layer 160 fills in the space between conduits 150, the space between conduits 150 and separator assembly 120, and the space between cover 170 and conduits 150. Insulation 180 is wrapped around cover 170 and directly engages cover 170.

Figure 5:
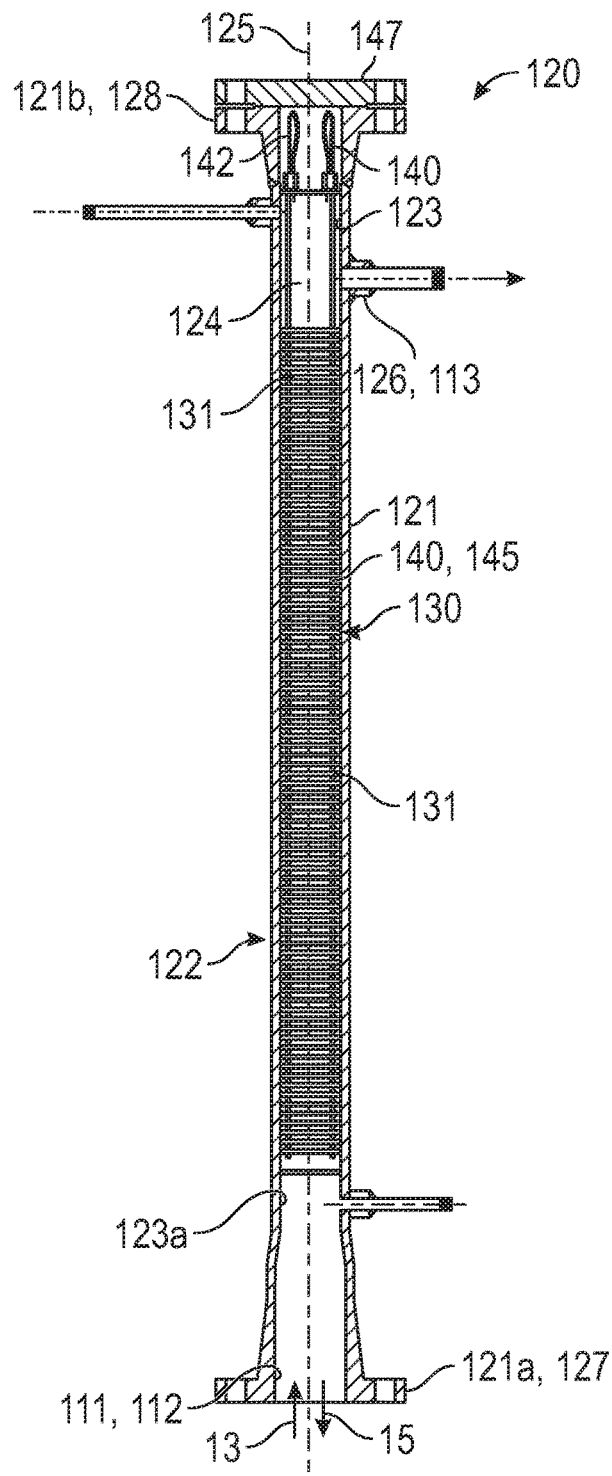
FIG. 5 is a cross-sectional view of the separator assembly of the fluid conditioner of FIG. 2.
Figure 6:
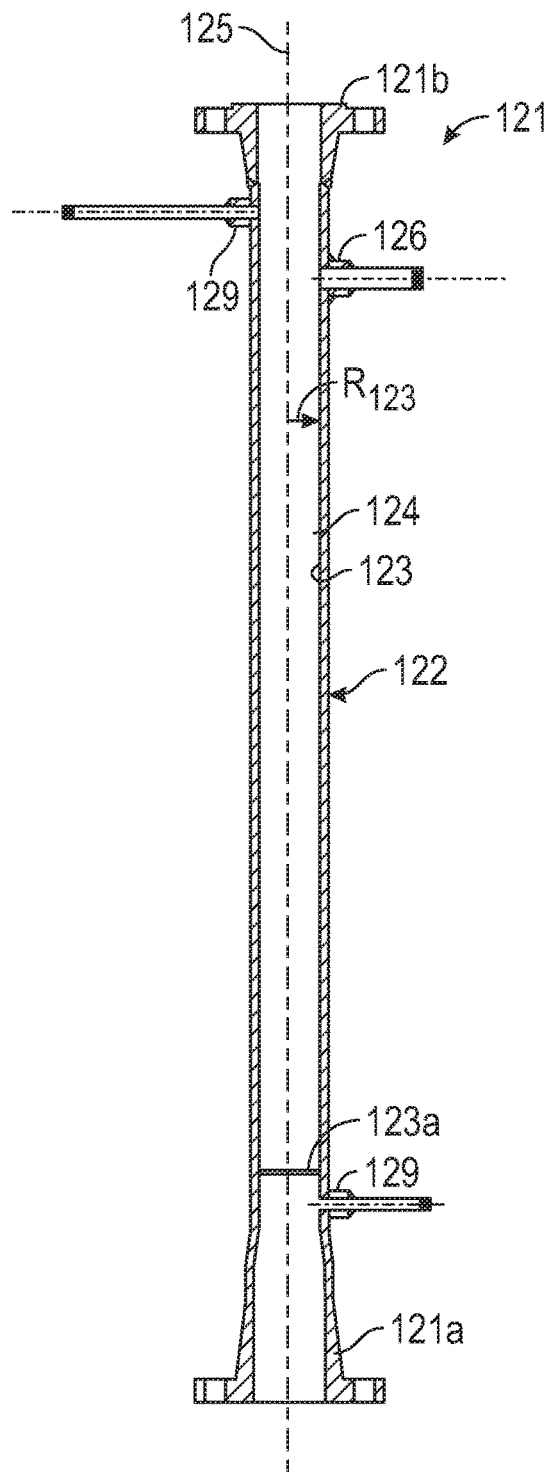
FIG. 6 is a cross-sectional view of the fluid conduit of the separator assembly of FIG. 5.

Referring now to FIG. 5, separator assembly 120 includes a radially outer tubular conduit 121 and a baffle assembly 130 coaxially disposed within conduit 121. As best shown in FIGS. 5 and 6, conduit 121 has a central or longitudinal axis 125, a first or lower end 121a, a second or upper end 121b, a radially outer surface 122 extending axially between ends 121a, 121b, and a radially inner surface 123 extending axially between ends 121a, 121b. Inner surface 123 defines a throughbore or passage 124 that extends axially between ends 121a, 121b. An annular lip or shoulder 123a is provided along inner surface 123 proximal lower end 121a. As will be described in more detail below, shoulder 123a supports baffle assembly 130 within conduit 121.

Conduit 121 also includes a port 126 that extends radially from passage 124 through surfaces 122, 123. In this embodiment, surfaces 122, 123 are cylindrical surfaces. In particular, inner surface 123 is disposed at a radius $R_{123}$ measured radially from axis 125. When separator 110 is assembled as shown in FIG. 2, axes 115, 125 are coaxially aligned, and ends 121a, 121b of conduit 121 define ends 110a, 110b, respectively, of separator 110.

Referring now to FIGS. 3-6, in this embodiment, each end 121a, 121b comprises a mounting flange 127, 128, respectively. Lower flange 127 couples fluid separator 110 to other device(s) and/or fluid conduit(s) positioned upstream of separator 110 relative to the flow of sample 13, thereby allowing flow into and out of passage 124 at lower end 121a. A cap 147 is secured to upper flange 128, thereby closing off passage 124 at upper end 121b.

As will be described in more detail below, during sampling operations, fluid sample 13 enters separator 110 and passage 124 at lower end 121a of conduit 121, sample 13 is separated into gas 14 and contaminants 15 within passage 124, gas 14 in passage 124 exits passage 124 and separator 110 via port 126, and contaminants 15 within passage 124 exit passage 124 and separator 110 via lower end 121a. In other words, lower end 121a functions as both an inlet and an outlet. Thus, lower end 121a of conduit 121 defines a sample inlet 111 and a contaminant outlet 112 of separator 110, and port 126 defines a conditioned gas outlet 113 of separator 110.

As best shown in FIGS. 5 and 6, conduit 121 also includes a plurality of sensor ports 129, each port 129 extends radially through conduit 121 and providing access to passage 124. Each sensor port 129 accommodates a temperature sensor 148 that measures and communicates the temperature of fluids within passage 124 (e.g., sample 13, gas 14, and contaminants 15). In this embodiment, one sensor port 129 is axially positioned proximal upper end 121b and another sensor port 129 is axially positioned proximal lower end 121a. For purposes of clarity and further explanation, sensor port 129 and corresponding temperature sensor 148 positioned proximal upper end 121b may be referred to as upper sensor port 129 and upper temperature sensor 148, respectively; and sensor port 129 and corresponding temperature sensor 148 positioned proximal lower end 121a may be referred to as lower sensor port 129 and lower temperature sensor 148. Upper sensor port 129 is axially positioned between flange 128 and gas outlet 113, and angularly spaced 180° from gas outlet 113. Thus, upper sensor port 129 and upper temperature sensor 148 are positioned above gas outlet 113 and on the opposite side of conduit 121. Lower sensor port 129 is axially positioned between shoulder 123a and flange 127, and angularly aligned with gas outlet 113. Thus, lower sensor port 129 and lower temperature sensor 148 are positioned proximal sample inlet 111 and on the same side of conduit 121 as gas outlet 113.

Figure 7:
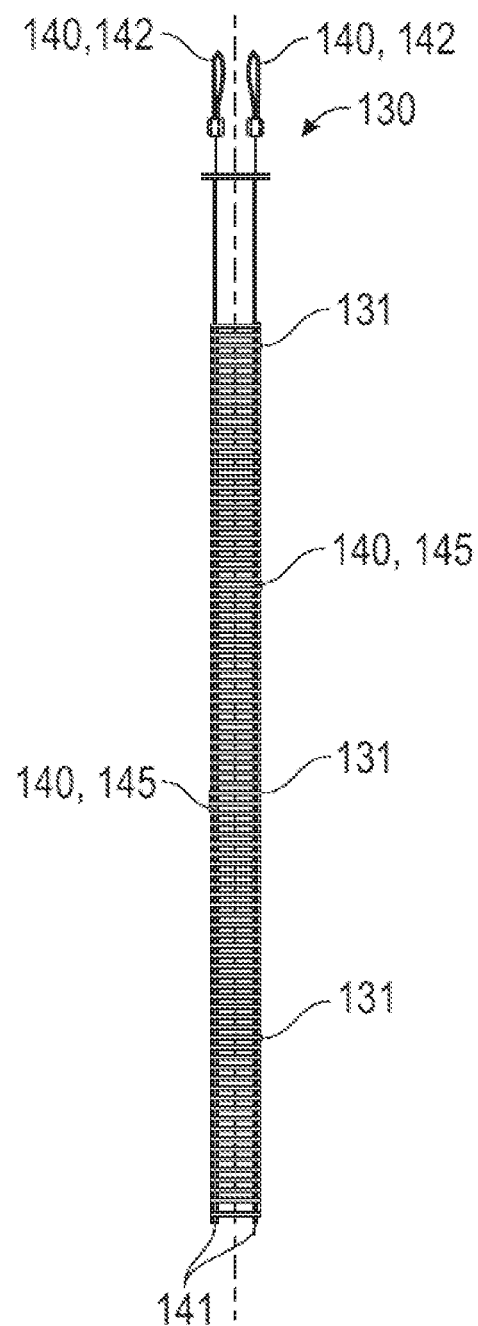
FIG. 7 is a side view of the baffle assembly of the separator assembly of FIG. 5.
Figure 8:
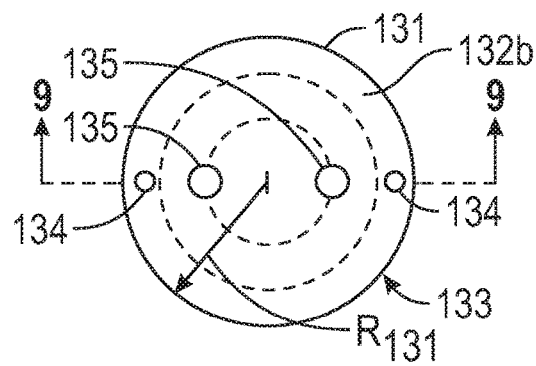
FIG. 8 is a top view of one of the baffles of the baffle assembly of FIG. 7.
Figure 9:
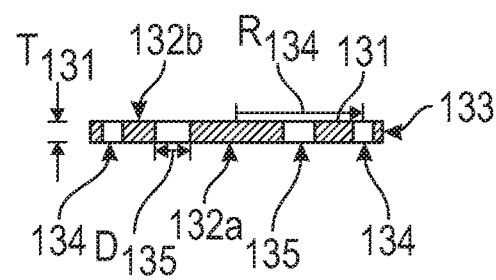
FIG. 9 is a cross-sectional side view of the baffle of FIG. 8 taken in section 9-9 of FIG. 8.
Figure 10:
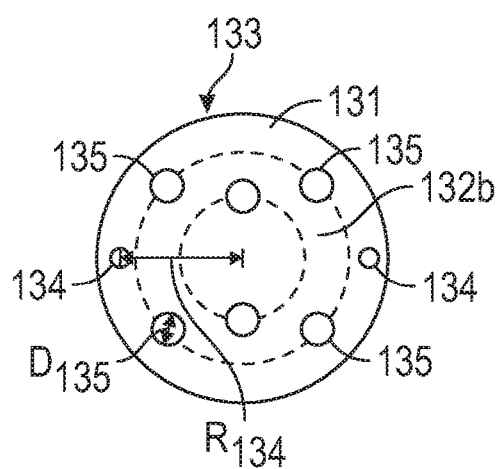
FIG. 10 is a top view of one of the baffles of the baffle assembly of FIG. 7.
Figure 11:
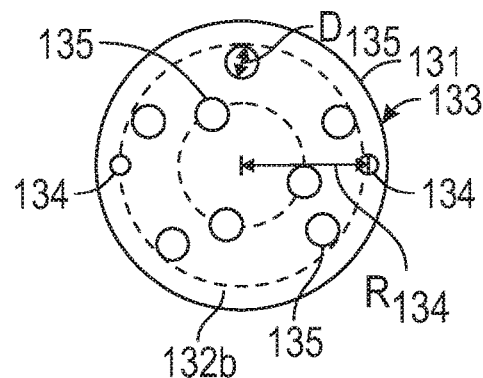
FIG. 11 is a top view of one of the baffles of the baffle assembly of FIG. 7.

Referring now to FIGS. 5 and 7, baffle assembly 130 includes a plurality of baffles 131, a top plate 136, a plurality of flexible cables 140 extending through baffles 131 and top plate 136, and a plurality of spacers 145 for maintaining the spacing of top plate 136 and baffles 131. As best shown in FIG. 5, top plate 136 is positioned above port 126, whereas the all the baffles 131 are positioned below port 126. Baffle assembly 130 has a central longitudinal axis generally coaxially aligned with axes 115, 125 when baffle assembly 130 is seated in conduit 121.

In this embodiment, two uniformly circumferentially-spaced cables 140 are provided. Thus, cables 140 are angularly spaced 180° apart from each other. Spacers 145 are rigid tubulars slidably mounted to cables 140 between each pair of adjacent baffles 131 and between top plate 136 and the uppermost baffle 131. In particular, one spacer 145 is disposed about each cable 140 between each pair of axially adjacent baffles 131 and between top plate 136 and the uppermost baffle 131. The two spacers 145 positioned between any given pair of axially adjacent baffles 131 have the same axial height to ensure baffles 131 remain in the vertical, stacked arrangement. The two spacers 145 positioned between top plate 136 and the uppermost baffle 131 have a greater axial height, and thus, the distance between top plate 136 and the uppermost baffle 131 is greater than the distance between any pair of axially adjacent baffles 131.

A terminal end cap 141 is fixably secured to the lower end of each cable 140 to prevent baffles 131 and spacers 145 from sliding off cables 140. In addition, the upper end of each cable 140 is formed into a loop 142, which enables an operator to position and manipulate baffle assembly 130 as it is installed in or removed from conduit 121.

Referring still to FIG. 5, to install baffle assembly 130 in conduit 121 to form separator assembly 120, cap 147 is removed from upper end 121a of conduit 121 to provide access to passage 124 via upper end 121a. Next, baffle assembly 130 is lifted and supported via loops 142 by an operator, and then lowered into passage 124 until the lowermost baffle 131 is seated against shoulder 123a. With the lowermost baffle 131 seated against shoulder 123a, the weight of baffle assembly 130 is shifted from cables 140 to conduit 121, thereby allowing the operator to release loops 142 and re-attach cap 147 to upper end 121a to form separator assembly 120. In particular, the weight of baffle assembly 130 is transferred through baffles 131 and spacers 145 to the lowermost plate 131', which is directly supported by shoulder 123a. As best shown in FIG. 5, when baffle assembly 130 is disposed in conduit 121, baffles 131 are axially-spaced and stacked one above-the-other, and cables 140 are oriented parallel to axes 115, 125 but radially offset and spaced from axes 115, 125. In addition, as previously described, top plate 136 is positioned above port 126 while the baffles 131 are positioned below port 126. Removal of baffle assembly 130 from conduit 121 is achieved by performing the installation process in reverse order.

It should be appreciated that flexible cables 140 allow some flexing of baffle assembly 130 as it is inserted into and withdrawn from conduit 121. In particular, baffle assembly 130 can flex along its central longitudinal axis at least 90° such that the central longitudinal axis of baffle assembly 130 at its upper end is horizontally oriented while the central longitudinal axis of baffle assembly 130 at its lower end is vertically oriented. Such flexing provides advantages in applications where overhead space (i.e., the space above fluid condition 100) is limited due to the presence of other equipment. In other words, the ability of baffle assembly 130 to bend and flex substantially reduces the vertical clearance above conduit 121 needed to install and remove baffle assembly 130 from conduit 121. In addition, the flexibility of baffle assembly 130 allows the individual baffles 131 to move laterally to a limited degree relative to each other, which may enhance contact between the individual baffles 131 and conduit 121, thereby offering the potential for increased heat transfer between baffle assembly 130 and conduit 121. It should also be appreciate that the plurality of parallel cables 140 passing through baffles 131 also restrict and/or prevent the individual baffles 131 from rotating relative to each other about the central longitudinal axis of the baffle assembly 130 during and after installation of the baffle assembly 130 in the conduit 121.

In general, the components of separator assembly 120 (e.g., conduit 121, baffles 131, cables 140, and spacers 145) may comprise any suitable materials such as metal(s) and metal alloys (e.g., aluminum, steel, etc.), non-metals (e.g., ceramics, polymers, etc.), composites, or combinations thereof. However, the components of separator assembly 110 preferably comprise rigid, durable materials that are capable of withstanding extended period of exposure to the relatively harsh conditions (e.g., temperatures, corrosive effects, etc.) imposed by unconditioned sample 13. Examples of suitable materials for the components of separator assembly 110 include stainless steel (e.g., 316 stainless steel), nickel alloys and superalloys (e.g., Monel, Monel 400, Inconel, Inconel 625, Hastelloy® from Haynes international, Inc., etc.), tantalum and tantalum alloys, titanium and titanium alloys, or combinations thereof. In this embodiment, the components of separator assembly 120 are made from 316 stainless steel.

Referring now to FIGS. 8-11, three exemplary baffles 131 of baffle assembly 130 are shown. Each baffle 131 is a round, flat disc or plate with a planar lower surface 132a, a planar upper surface 132b oriented parallel to surface 132a, a radially outer cylindrical surface 133 extending between surfaces 132a, 132b, a first plurality of cable holes 134 extending axially between surfaces 132a, 132b, and a second plurality of fluid orifices 135 extending axially between surfaces 132a, 132b. In addition, each baffle 131 has an outer radius $R_{131}$ and a thickness $T_{131}$. In this embodiment, each baffle 131 has the same outer radius $R_{131}$ and thickness $T_{131}$. In particular, the radius $R_{131}$ of each baffle 131 is the same or slightly less than (e.g., <5% less than) the inner radius $R_{123}$ of conduit 121. Accordingly, as best shown in FIG. 5, cylindrical outer surfaces 133 of baffles 131 slidingly engage cylindrical inner surface 123 of conduit 121 when baffle assembly 130 is disposed within conduit 121. The thickness $T_{131}$ of each baffle 131 is preferably about 1/16 in. to about 1/4 in. In this embodiment, outer radius $R_{131}$ is 1.14 in. and thickness $T_{131}$ is 1/8 in.

Referring now to FIGS. 8-11, each baffle 131 includes two cable holes 134 and at least two fluid orifices 135. Cable holes 134 in each baffle 131 are uniformly circumferentially-spaced. Since two holes 134 are provided in each baffle 131, holes 134 are angularly spaced 180° apart. In addition, each hole 134 is positioned at the same radius $R_{134}$ measured from the centers of baffles 134, which is coincident with axis 125 when baffle assembly 130 is disposed in conduit 121. In this embodiment, cable holes 134 in each baffle 131 are positioned proximal the outer periphery of the baffle 131. In particular, radius $R_{134}$ of each hole 134 is preferably at least 70% of the radius $R_{131}$ and more preferably at least 80% of the radius $R_{131}$.

Similar to baffles 131, top plate 136 is a round, flat disc or plate with a planar lower surface, a planar upper surface, and a radially outer cylindrical surface that slidingly engage cylindrical inner surface 123 of conduit 121 when baffle assembly 130 is disposed within conduit 121. In addition, top plate 136 includes two cable holes 134 to allow cables 140 to pass therethrough. However, unlike baffles 131, top plate 136 does not include any fluid orifices or other holes.

Referring now to FIGS. 5 and 7, as previously described, cables 140 extend through baffles 131 and top plate 136. In particular, each cable 140 extends through one cable hole 134 in each baffle 131 and top plate 136. Baffles 131 and top plate 136 are arranged in baffle assembly 130 such that cables holes 134 are coaxially aligned. The positioning and spacing of holes 134 in baffles 131 and top plate 136 enable the 180° angular spacing of cables 140 and the positioning of cables 140 proximal the outer periphery of baffles 131, proximal the outer periphery of top plate 136, and proximal inner surface 123 of conduit 121 (i.e., radially offset from axis 125 as previously described). Each cable hole 134 has a diameter that is substantially the same or slightly greater than the outer diameters of cables 140. Thus, cables 140 slidingly engage baffles 131 and top plate 136 when disposed in holes 134, and further, restrict and/or prevent fluid flow through holes 134. Consequently, fluids flowing through conduit 121 primarily flow through orifices 135 as opposed to cable holes 134. Since top plate 136 lacks fluid orifices 135, top plate 136 generally blocks or restricts the flow of fluids therethrough, thereby directing fluids flowing upward within conduit 121 toward port 126. To enable sufficient flexing of baffle assembly 130 as described above, each cable 140 preferably has a diameter of about $1/16^{th}$ in. to 1/4 in., with each cable hole 134 having a corresponding diameter to slidingly receive and accommodate a cable 140. In this embodiment, each cable 140 has a diameter of $1/8^{th}$ in.

Referring again to FIGS. 8-11, a plurality of fluid orifices 135 are provided in each baffle 130. Each fluid orifice 135 has a diameter $D_{135}$ that is greater than the diameter of cables holes 134 and cables 140. The diameter $D_{135}$ of each fluid orifice 135 is preferably 1/8 in. to 1/2 in. In this embodiment, diameter $D_{135}$ of each fluid orifice is 1/4 in. Although each orifice 135 has the same diameter $D_{135}$ in this embodiment, the number of fluid orifices 135 in different baffles 131 may vary. In general, the number of orifices 135 in baffles 131 decreases moving upward along baffle assembly 130. More specifically, in this embodiment, baffle assembly 130 includes eighty-three baffles 131. Moving upward along baffle assembly 130, the baffles 131 are arranged as follows: the first pair of baffles 131 (the bottom two baffles 131) each include twenty-two fluid orifices 135; the next ten baffles 131 each include ten fluid orifices 135; the next ten baffles 131 each include eight fluid orifices 135; the next ten baffles 131 each include six fluid orifices 135; the next ten baffles 131 each include four fluid orifices 135; and the next forty baffles 131 (the top fourty baffles 131) each include two fluid orifices 135. As previously described, the top plate 136 includes no fluid orifices 135. Referring still to FIGS. 5 and 7, fluid orifices 135 in each pair of axially adjacent baffles 131 are radially and/or circumferentially offset such that no orifices 135 in axially adjacent baffles 131 are coaxially aligned. Such arrangement of baffles 131 and fluid orifices 135 generates a more tortuous path for fluids flowing through passage 124 of conduit 121.

As will be described in more detail below, fluid orifices 135 allow fluid within passage 124 of conduit 121 to flow axially through each baffle 131. In particular, orifices 135 allow unconditioned sample 13, typically in a gaseous phase with some suspended particulate matter, to flow through inlet 121a into separator assembly 120 and allow contaminants 15, typically in a liquid phase, to flow axially downward through outlet 121a and out of separator assembly 120. Further, orifices 135 allow conditioned gas 14 to flow through passage 124 to port 126, and out of separator assembly 121 via outlet 113.

Referring now to FIGS. 3 and 4, in this embodiment, cooling conduits 150 extend helically about conduit 121. Consequently, cooling conduits 150 have a helical shape and may be referred to herein as helical cooling coils 150. In particular, helical cooling coils 150 are wrapped tightly around conduit 121 such that coils 150 directly contact and engage outer surface 122 of conduit 121. In some embodiments, a thin coating of a thermally conductive material (e.g., the thermally conductive epoxy used to form layer 160) may be applied to outer surface 122 of conduit 121 along the portion of surface conduit 121 wrapped with coils 150. In addition, coils 150 are axially compressed such that axially adjacent turns of coils 150 directly contact each other. In this embodiment, two helical cooling coils 150 are provided, and further, coils 150 are intermeshed. In other words, adjacent turns of a given coil 150 are axially spaced apart with one turn of the other coil 150 is disposed therebetween. As best shown in FIG. 3, to hold coils 150 in the desired position during manufacturing, coils 150 are tack welded to outer surface 122 of conduit 121 at a plurality of attachment points 152.

As best shown in FIG. 3, in this embodiment, coils 150 extend axially along substantially the entire length of conduit 121. In particular, coils 150 extend axially from an upper position along conduit 121 immediately above port 126 to a lower position along conduit 121 proximal lower flange 127.

Referring again to FIGS. 3 and 4, each coil 150 is an elongate tubular having a first or upper end 150a, a second or lower end 150b, and an inner throughbore or flow passage 151 extending between ends 150a, 150b. As will be described in more detail below, coils 150 are used to cool conduit 121 and the fluids therein (e.g., sample 13). In particular, a cooling fluid or medium 153 flows into passage 151 of each coil 150 at its upper end 150a and out of passage 151 of each coil 150 at its lower end 150b. As best shown in FIG. 2, a cooling device 155 is provided at end 150a of each coil 150 to cool the cooling fluid 153 as it enters the coil 150. Due to a temperature difference between the relatively hot sample 13 in conduit 121 and the relatively cold cooling fluid 153, thermal energy is transferred from the sample 13 through conduit 121 and coils 150 to the cooling fluid 153, thereby reducing the temperature of sample 13 within conduit 121. To enhance the transfer of thermal energy between conduit 121 and coils 150, the contact surface area between coils 150 and outer surface 122 of conduit 121 is maximized as described above, and further, coils 150 are made of a material having a relatively high thermal conductivity such as copper or aluminum. In this embodiment, coils 150 are made of copper. Upon exiting coils 150 at ends 150b, the cooling fluid 153 can be exhausted to the environment, or returned to the cooling devices 155, re-cooled, and then recirculated back through coils 150.

As previously described, cooling fluid 153 enters passages 151 at ends 150a and exits passages 151 at ends 150b. Accordingly, each end 150a defines an inlet 156 to each coil 150 and each end 150b defines an outlet 157 of each coil 150. In general, each cooling device 155 may comprise any suitable device capable of reducing the temperature of a cooling fluid 153 including, without limitation, a thermoelectric cooling device. In addition, cooling fluid 153 can be any suitable type of cooling medium (liquid and/or gas) including, without limitation, air, water, propane or Freon®. In this embodiment, each cooling device 155 is a 1,000 BTU (15 SCFM of air) Vortex Cooler™ available from ITW Air Management Co. of Cincinnati, Ohio, and Vortex Koolers available from Rittal Corporation of Urbana, Ohio. To enable a sufficient volumetric flow of cooling fluid 153 and associated cooling, each coil 150 preferably has an inner diameter of 0.32 in. to 0.625 in. and an outer diameter of ⅜ in. and ½ in.

Referring now to FIG. 4, thermally conductive layer 160 surrounds and encapsulates coils 150 and extends radially between conduit 121 and protective cover 170. Layer 160 is designed to be thermally conductive to facilitate the transfer of thermal energy between tubular conduit 121 and coils 150. In this embodiment, layer 160 is a thermally conductive epoxy that is applied in a liquid state (e.g., brushed on) and then allowed to cure and harden around cooling coils and tubular conduit 121. Thus, in this embodiment, layer 160 may be described as being formed "in-situ." In this embodiment, layer 160 is made of thermally conductive epoxy adhesive TC-2810 available from 3M™ of Maplewood, Minn. The thermally conductive epoxy adhesive TC-2810 has a thermal coefficient of expansion of 62×10−6/° C. at 23° C. and 205×10−6/° C. at 120° C.; a thermal conductivity of 0.80 to 1.4 w/m-° K; a thermal impedance of 0.05° C. in$^2$/W (2 mil); a dielectric strength of 750 volts/mil; a dielectric constant of 4.6; and hydrocarbon outgassing <25 ug/g.

As previously described, a thin coating of the thermally conductive epoxy used to form layer 160 can be applied to outer surface 122 of conduit 121 before mounting coils 150 such that a thin layer of the thermally conductive epoxy is radially positioned between coils 150 and conduit 121. After wrapping coils 150 around conduit 121, the thermally conductive epoxy is applied to coils 150 to fill in any air gaps between coils 150, and then applied to completely coat and encase coils 150. In embodiments described herein, the radial thickness of the portion of thermally conductive layer 160 extending radially from coils 150 (i.e., the radial thickness of layer 160 disposed on top of coils 150) is preferably at least ⅛ in.

Figure 12:
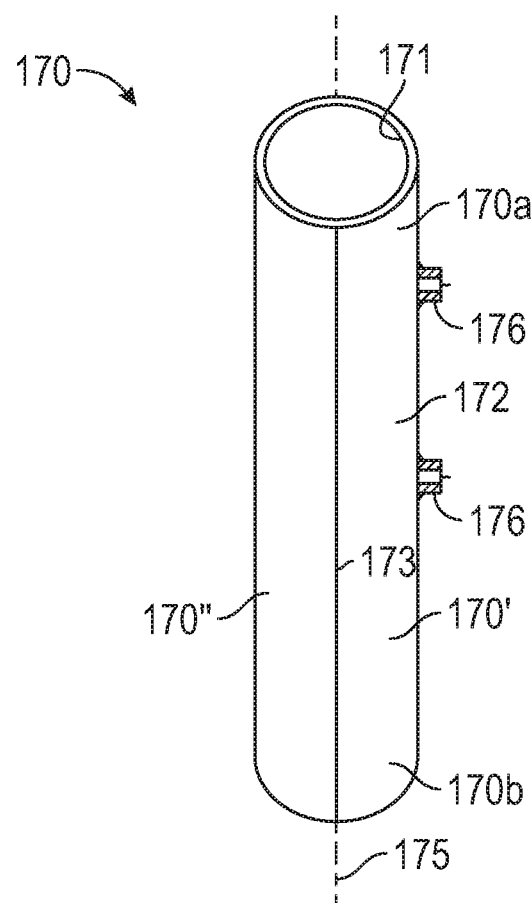
FIG. 12 is a perspective view of the protective cover of the fluid conditioner of FIG. 2.
Figure 13:
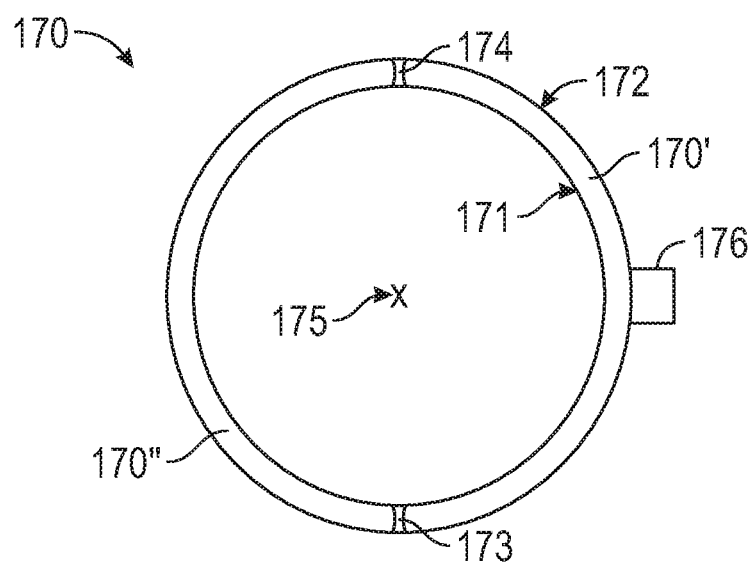
FIG. 13 is a top view of the protective cover of FIG. 12.

Referring now to FIGS. 2, 4, 12, and 13, protective cover 170 is disposed about layer 160 and coils 150 are embedded within layer 160. Cover 170 is an elongate tubular having a central or longitudinal axis 175, a first or upper end 170a, a second or lower end 170b, a cylindrical radially inner surface 171 extending axially between ends 170a, 170b, and a cylindrical radially outer surface 172 extending axially between ends 170a, 170b. As best shown in FIGS. 12 and 13, in this embodiment, cover 170 is made from two semi-cylindrical halves 170', 170" that are welded together along seams 173, 174 that are angularly spaced 180° apart.

Cover 170 protects the components disposed therein (e.g., coils 150) from inadvertently being damaged (e.g., shields these components from impact loads). Accordingly, cover 170 is preferably made of a durable rigid material such as steel, stainless steel, copper, or aluminum. Cover 170 also provides a base to which sample monitoring and control system 190 can be securely coupled. In this embodiment, a pair of axially spaced mounts or connectors 176 extend radially from half 170" of cover 170. Connectors 176 provide a means for securing sample monitoring and control system 190 to separator 110.

Insulation 180 surrounds cover 170 and insulates the components disposed therein. In general, insulation 180 functions to limit the transfer of thermal energy between coils and the surrounding environment to facilitate the transfer of thermal energy between sample 13 in conduit 121 and cooling fluid 153 in coils 150. In general, insulation 180 can be any suitable insulation known in the art that can be wrapped around cover 170. In this embodiment, insulation 180 is an Ecofoil insulation blanket available from Eco-Foil® of Urbana, Iowa.

Referring again to FIG. 1, sample monitoring and control system 190 includes a plurality of temperature sensors, a plurality of flow control valves and corresponding actuators that work together to monitor and control the conditioning of the fluid sample 13 within separator 110. The information acquired by system 190 during sampling operations is communicated to a computer system, by hardwire or wirelessly, where it may be monitored by plant operators. In general, the computer system may be on-site or remote from the processing operations. In response to the acquired information, the computer system and/or plant operators may make various adjustments to the separation process via the control valves and valve actuators.

In this embodiment, system 190 includes upper temperature sensor 148, lower temperature sensor 148, a temperature sensor 149 for each cooling device 155 and corresponding inlet 156, and a temperature sensor 149 for each outlet 157. Upper temperature sensor 148 measures and communicates the temperature of conditioned gas 13 proximal upper end 121b. Lower temperature sensor 148 measures and communicates the temperature of sample fluid 13. Temperature sensors 149 measure the temperature of the cooling fluid 153—the two sensors 149 at inlets 156 measure the temperature of cooling fluid 153 at inlets 156, and the two sensors 149 at outlets 157 measure the temperature of cooling fluid 153 at outlets.

System 190 also includes a control valve 191 and associated valve control actuator 192 for each cooling device 155, and a control valve 193 and associated valve control actuator 194 for gas outlet 113. Valve control actuators 192, via valves 191, control the flow of cooling fluid 153 into cooling devices 155 and inlets 156 of coils 150 of separator 110. In particular, valves 191 are in an opened position, cooling fluid 153 flows to cooling devices 155 and inlets 156, however, when valves 191 are in a closed position, cooling fluid 153 is restricted and/or prevented from flowing to cooling devices 155 and inlets 156. Valve control actuators 192 actuate valves 191 between the opened position and the closed position. Further, as each valve 191 includes its own actuator 192, each valve 191 can be independently controlled. Each cooling device 155 also includes a cooling device actuator 158 that independently controls whether the particular cooling device 155 is on or off, as well as the degree of cooling power output by each cooling device 155.

Actuators 194, via valve 193, controls the flow of conditioned gas 14 through outlet 113 of separator 110. In particular, valve 193 is in an opened position, conditioned gas 14 flows from separator 110 to analytical instrumentation 30, however, when valve 193 is in a closed position, conditioned gas 14 is restricted and/or prevented from flowing through outlet 113 from separator 110 to analytical instrumentation 30. Valve control actuator 194 actuates valves 193 between the opened position and the closed position. In general, each control actuators (e.g., actuators 192, 194, 158) may be any suitable type of actuator including, without limitation, electronic, hydraulic, or pneumatic actuators.

By employing the temperature sensors (e.g., temperature sensors 148, 149), valves (e.g., valves 191, 193), and actuators (e.g., actuators 192, 194, 158) previously described, system 190 is capable of acquiring, real-time, (a) the temperature of cooling fluid 153 at each inlet 156 and at each outlet 157; (b) the temperature of conditioned gas 14 at outlet 113; (c) the status and position of each valve 191, 193 (e.g., open, closed, etc.); and (d) the status of each cooling device 155 (e.g., on, off, etc.). In addition, by controlling valves 191 and cooling devices 155 with actuators 192, 158, respectively, system 190 is capable of controlling the temperature of cooling fluid 153 at inlets 156, which in turn allows system 190 to control the temperature of cooling fluid 153 within coils 150 and outlets 157, as well as control the temperature of fluids 13, 14. Still further, by controlling valve 193 with actuator 194, system 190 is capable of controlling the flow of conditioned gas 14 flowing from separator 110 to analytical instrumentation 30.

Referring now to FIG. 2, in this embodiment, the components of system 190 (e.g., valves 191, 193, associated actuators 192, 194, and temperature sensors 148, 149, etc.) are disposed in a housing 195 coupled to separator 110. Further, the cabling for temperature sensors 148, 149 and actuators 158, 192, 193 is routed to housing 195). The information acquired with system 190 (i.e., the temperature of cooling fluid 153 at inlets 156 and outlets 157 of coils 150; the status and position of valves 191, 193; the status and cooling power of cooling devices 155; and the temperature of conditioned gas 14), is communicated from housing 195 to the control room, and conditioned gas 14 is communicated to analytical instrumentation 30.

Referring again to FIG. 1, during sampling operations, cooling devices 155 are turned on with actuators 158, and valve 191 for each cooling device 155 is maintained in the opened position with the corresponding actuator 192. As a result, cooling fluid 153 flows through valves 191 to cooling devices 155, which reduces the temperature of the cooling fluid 153. The temperature of cooling fluid 153 at inlet 156 of each coil 150 is preferably −30° F. to 110° F., and more preferably 38° F. to 42° F. Inlet temperature sensors 149 measure the temperature of cooling fluid 153 at inlets 156, and based on the temperature of cooling fluid 153 at inlets 156, cooling devices 155 are controlled via actuators 158 to maintain, increase, or decrease the temperature of cooling fluid 153 as passing therethrough to achieve the desired temperature for cooling fluid 153 at inlets 156. Cooling fluid 153 is cooled by cooling devices 155 and flows through inlets 156 into coils 150, and then through helical coils 150 about conduit 121 to outlets 157. As cooling fluid 153 flows through coils 150, it cools coils 150 and thermally conductive layer 160, both of which directly contact conduit 121. Simultaneously, unconditioned fluid sample 13 is pulled from bulk fluid stream 12. The fluid stream 12, and hence the unconditioned fluid sample 13, may have a temperature as high as 700° F. (e.g., a bulk decoke fluid stream typically has a temperature of 350 to 700° F.) and may be in a gaseous state with some suspended particulate matter. The unconditioned fluid sample 13 enters inlet 111 at the lower end 121*a* of conduit 121 and flows therethrough. Thus, conduit 121 is in direct contact with the relatively cold coils 150 and layer 160, and in direct contact with the relatively hot fluid sample 13. As a result, conductive heat transfer occurs between conduit 121, coils 150, and layer 160. In particular, thermal energy in fluid sample 13 is transferred across conduit 121, layer 160, and coils 150, and into cooling fluid 153, thereby increasing the temperature of cooling fluid 153 as it moves through coils 150, and decreasing the temperature of fluid sample 13 as it migrates upwardly through conduit 121. In other words, the temperature of cooling fluid 153 is coldest at inlets 156, steadily increase as it moves helically about conduit 121 and axially downward through coils 150 toward outlets 157, and is warmest at outlets 157; and the temperature of fluid sample 13 is greatest at inlet 111, decreases steadily migrating axially upward through conduit 121, and is coolest at conditioned gas outlet 113. Thus, separator 110 transfers thermal energy from fluid sample 13 into cooling fluid 153.

Referring now to FIGS. 1 and 5, the unconditioned fluid sample 13 enters inlet 111 at the lower ends 110*a*, 121*a* and migrates upward through conduit 121. Upon entry into conduit 121, unconditioned fluid sample 13 contacts conduit 121 and baffles 131. Within separator 110, unconditioned fluid sample 13 has its maximum temperature at inlet 111. As previously described, conduit 121 is cooled via direct contact with coils 150 and layer 160. In addition, baffles 131, which are in direct contact with conduit 121, are cooled via direct contact with conduit 121. As a result, conduit 121 and baffles 131 have temperatures that are less than unconditioned fluid sample 13 at inlet 111. As unconditioned fluid sample 13 contacts conduit 121 and baffles 131, it is cooled and flows through fluid orifices 135 in baffles 131. In general, unconditioned fluid sample 13 is free to flow through fluid orifices 135 in baffles 131. However, since orifices 135 in axially adjacent baffles 131 are out of alignment, the unconditioned fluid sample 13 is urged to move radially outward or inward when it encounters lower surface 132*a* of each baffle 131. As a result, the majority of unconditioned fluid sample 13 is generally guided or funneled towards fluid orifices 135 as the relatively hot unconditioned fluid sample 13 inherently wants to rise axially upward within passage 124.

Similar to conduit 121, the temperature of baffles 131 is less than the temperature of unconditioned fluid sample 13. As fluid sample 13 flows along conduit 121 and across baffles 131, thermal energy is transferred from the relatively warmer sample fluid 13 to the relatively cold conduit 121 and baffles 131, and the temperature of fluid sample 13 decreases. In addition, since fluid orifices 135 of axially adjacent baffles 131 are disposed at different angular positions about axes 115, 125, as unconditioned fluid sample 13 migrates upward through separator assembly 120, it is forced to change directions along a tortuous path. As a result, the speed of unconditioned fluid sample 13 gradually decreases and the pressure of unconditioned fluid sample 13 gradually increases as it migrates through separator assembly 120 from inlet 111 toward outlet 113. Thus, the pressure of unconditioned fluid sample 13 is greatest proximal outlet 113 and upper end 121*b*, which is also the region at which the temperature of unconditioned fluid sample 13, conduit 121, and baffles 131 are lowest. Such conditions (decreasing temperature and increase pressure of fluid sample 13) bring the molecules in unconditioned fluid sample 13 closer together and facilitate the coalescence of contaminants 15 (i.e., water and heavy hydrocarbons), which form relatively heavy liquid droplets that drain and flow under the force of gravity downward along surfaces 132*a*, 132*a*, 132*b* and through orifices 135 in baffles 131. Small quantities of the coalesced liquid contaminants 15 may also drip through any small passages in holes 134 between cables 140 and baffles 131. Particulate matter in fluid sample 13 may become captured in such droplets and flow axially downward along surfaces 132*a*, 132*a*, 132*b* and through orifices 135 with the droplets. Contaminants 15 flow along surfaces 132*a*, 132*a*, 132*b* and through orifices 135 to lower end 121*a*, and then exit conduit 121 via contaminant outlet 112 back into the bulk fluid stream 12. However, as contaminants 15 coalesce and drain, the remaining unconditioned fluid sample 13, which has been at least partially conditioned by the removal of some contaminants 15, continues to migrate upward through fluid orifices 135 to outlet 113.

In the manner previously described, unconditioned fluid sample 13 is gradually transformed into conditioned gas 14 by the gradual separation and removal of contaminants 15. Contaminants 15 are continuously separated and removed from unconditioned fluid sample 13 as it migrates through separator assembly 120. Although fluid sample 13 is described as "unconditioned" as it moves through separator assembly 120, and gas 14 is described as "conditioned" upon exiting separator assembly 120, it should be appreciated that fluid sample 13 is gradually conditioned along its entire migration through separator assembly 120, and is at its most "conditioned" state upon exiting separator assembly 120 via outlet 113.

As previously described, system 190 acquires real-time information relating to (a) the temperature of cooling fluid 153 at each inlet 156 and each outlet 157; (b) the temperature of conditioned gas 14 at upper end 121*b*; (c) the status and position of each valve 191, 193 (e.g., open, closed, etc.); and (d) the status of each cooling device 155 (e.g., on, off, etc.). In addition, by controlling valves 191 and cooling devices 155 with actuators 192, 158, respectively, system 190 is capable of controlling the temperature of cooling fluid 153 at inlets 156, which in turn allows system 190 to control the temperature of cooling fluid 153 within coils 150 and outlets 157, as well as control the temperature of fluid sample 13. Still further, by controlling valve 193 with actuator 194, system 190 is capable of controlling the flow of conditioned gas 14 flowing from separator 110 to analytical instrumentation 30. Further, as previously described, the separation and removal of contaminants 15 from unconditioned fluid sample 13 results from the cooling of unconditioned fluid sample 13, increasing the pressure of unconditioned fluid sample 13, and the coalescence of contaminants 15 into liquid droplets. Accordingly, the temperature of unconditioned fluid sample 13 as it migrates through separator assembly 120 is an important factor in the separation process—if the temperature of unconditioned fluid sample 13 is not sufficiently decreased in separator assembly 120, then there may not be adequate separation and removal of contaminants 15. Without sufficient separation and removal of contaminants 15, analytical instrumentation 30 may be fouled and/or damaged.

The temperature of cooling fluid 153 at inlets 156 is preferably maintained at −30° F. to 110° F., and more preferably 38° F. to 42° F. This temperature range for cooling fluid 153 results in sufficient heat transfer from unconditioned fluid sample 13 to achieve an acceptable temperature for unconditioned fluid sample 13 (i.e., a temperature sufficiently low to achieve the desired separation and removal of contaminants 15). In particular, a cooling fluid inlet temperature of −30° F. to 110° F., and more preferably 38° F. to 42° F. results in a conditioned gas 14 outlet temperature of 0° F. to 110° F., and more preferably 60° F. to 90° F. If the temperature of cooling fluid 153 at inlets 156, as measured by temperature sensors 149, is too low, the degree of cooling provided by cooling devices 155 may be decreased via actuators 158. On the other hand, if the temperature of cooling fluid 153 at inlets 156, as measured by temperature sensors 149, is too high, the degree of cooling provided by cooling devices 155 may be increased via actuators 158. In some instances, the temperature of unconditioned fluid sample 13 and conditioned gas 14 may still be too high. For example, the temperature of the bulk fluid stream 12 may unexpectedly spike, all cooling devices 155 may be operating at maximum capacity but still cannot achieve the preferred temperature for cooling fluid 153 at inlets 156. If the temperature of conditioned gas 14 at upper end 121*b*, as measured by upper temperature sensor 148, is sufficiently high, such that an insufficient quantity of contaminants 15 were separated and removed, then system 190 can actuate valve 193 to the closed position with actuator 194, thereby restricting and/or preventing conditioned gas 14 from flowing to analytical instrumentation 30.

Figure 14:
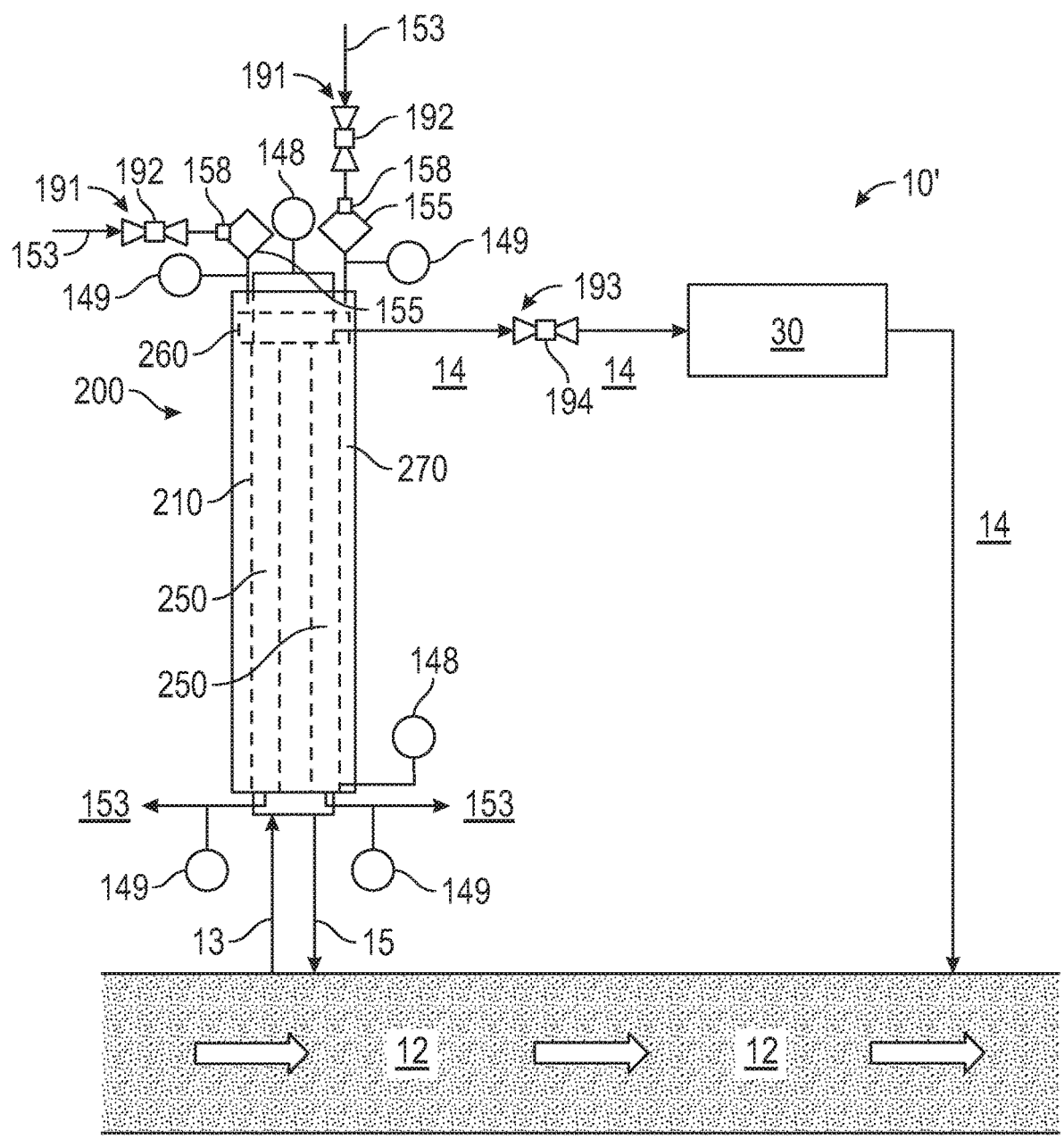
FIG. 14 is a schematic view of an embodiment of a system for sampling a bulk chemical or hydrocarbon fluid stream.

Referring now to FIG. 14, an embodiment of a system 10' for sampling a bulk fluid stream 12 is shown. System 10' is substantially the same as system 10 previously described and shown in FIG. 1 with the exception that fluid conditioner 100 is replaced with fluid conditioner 200 described in more detail below. Thus, system 10' includes fluid conditioner 200 and analytical instrumentation 30 as previously described downstream from conditioner 200. System 10' receives a sample 13 from the fluid stream 12 and conditions sample 13 with fluid conditioner 200 to remove contaminants 15 prior to being directed to analytical instrumentation 30. In particular, conditioner 200 separates sample 13 into contaminants 15, which are fed back to bulk fluid stream 12, and the remaining gas 14, which is passed on to analytical instrumentation 30 for analysis. After analysis, gas 14 is fed from instrumentation back into bulk fluid stream 12.

Similar to conditioner 100, conditioner 200 can be used in connection with any suitable chemical or hydrocarbon processing operation to separate contaminants 15 and gas 14 prior to analysis with instrumentation 30. In one exemplary embodiment, system 10' is employed to sample and analyze a decoke fluid sample from a hydrocarbon cracking operation to determine the ethylene and/or propylene yields during the cracking operations. In such embodiments, fluid sample 13 is an unconditioned decoke fluid sample comprising contaminants 15 (e.g., water, relatively heavy hydrocarbons (i.e., hydrocarbon molecules having six or more carbon atoms), and small quantities of particulate matter) and gas 14 comprises relatively light hydrocarbons (i.e., hydrocarbons molecules having five or less carbon atoms such as ethylene, propylene, methane, ethane, and propane).

Figure 15:
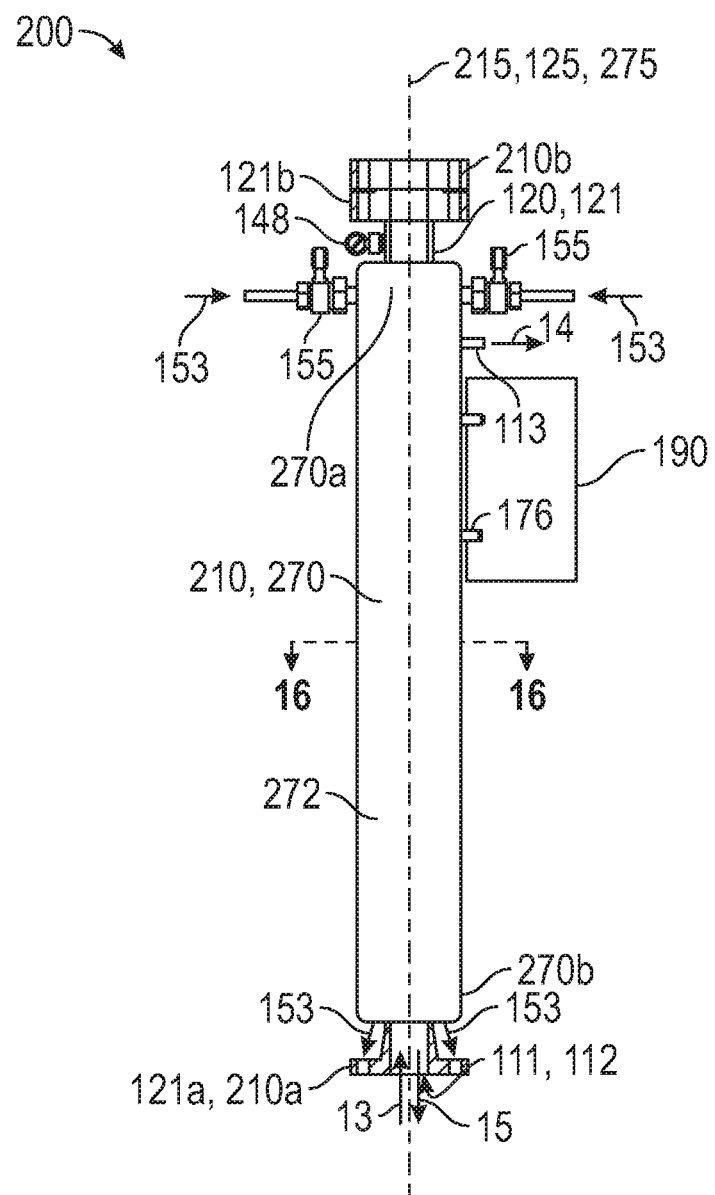
FIG. 15 is a side view of the fluid conditioner of FIG. 14.

Referring now to FIGS. 14 and 15, fluid conditioner 200 is similar to fluid conditioner 100 previously described with the exception that helical cooling conduits 150 are replaced with linear cooling conduits, the cooling fluid exiting the cooling devices is distributed to the cooling conduits with a manifold, and thermally conductive layer 160 is not provided. More specifically, conditioner 200 includes a fluid separator 210 and a sample monitoring and control system 190 coupled to separator 210. Sample monitoring and control system 190 is as previously described, and in FIG. 15, sample monitoring and control system 190 is schematically shown.

Similar to fluid separator 110 previously described, separator 210 utilizes distillation to separate contaminants 15 and gas 14. Namely, during conditioning with separator 210, fluid sample 13 is cooled, and as a result, gaseous contaminants 15 such as water and relatively heavy hydrocarbons phase change to liquid droplets that coalesce within separator 210. Although fluid sample 13 is cooled within separator 210 and gaseous contaminants 15 separate out as liquid, conditioned gas 14 remains a gas, albeit at a lower temperature than fluid sample 13. Thus, separator 210 may also be described as a distillation device or probe.

Figure 16:
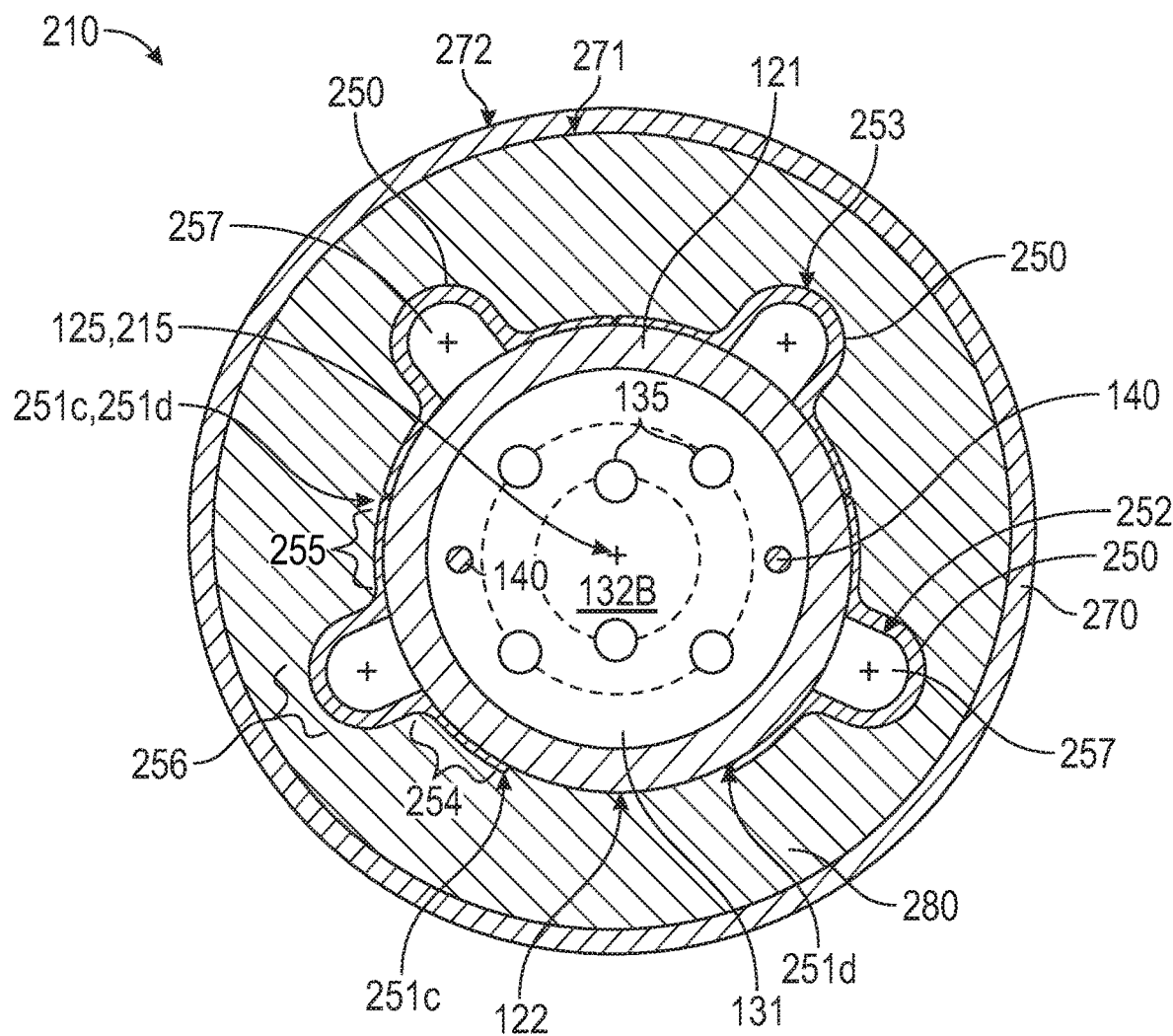
FIG. 16 is a cross-sectional top view of the fluid conditioner of FIG. 15 taken in section 16-16 of FIG. 15.
Figure 17:
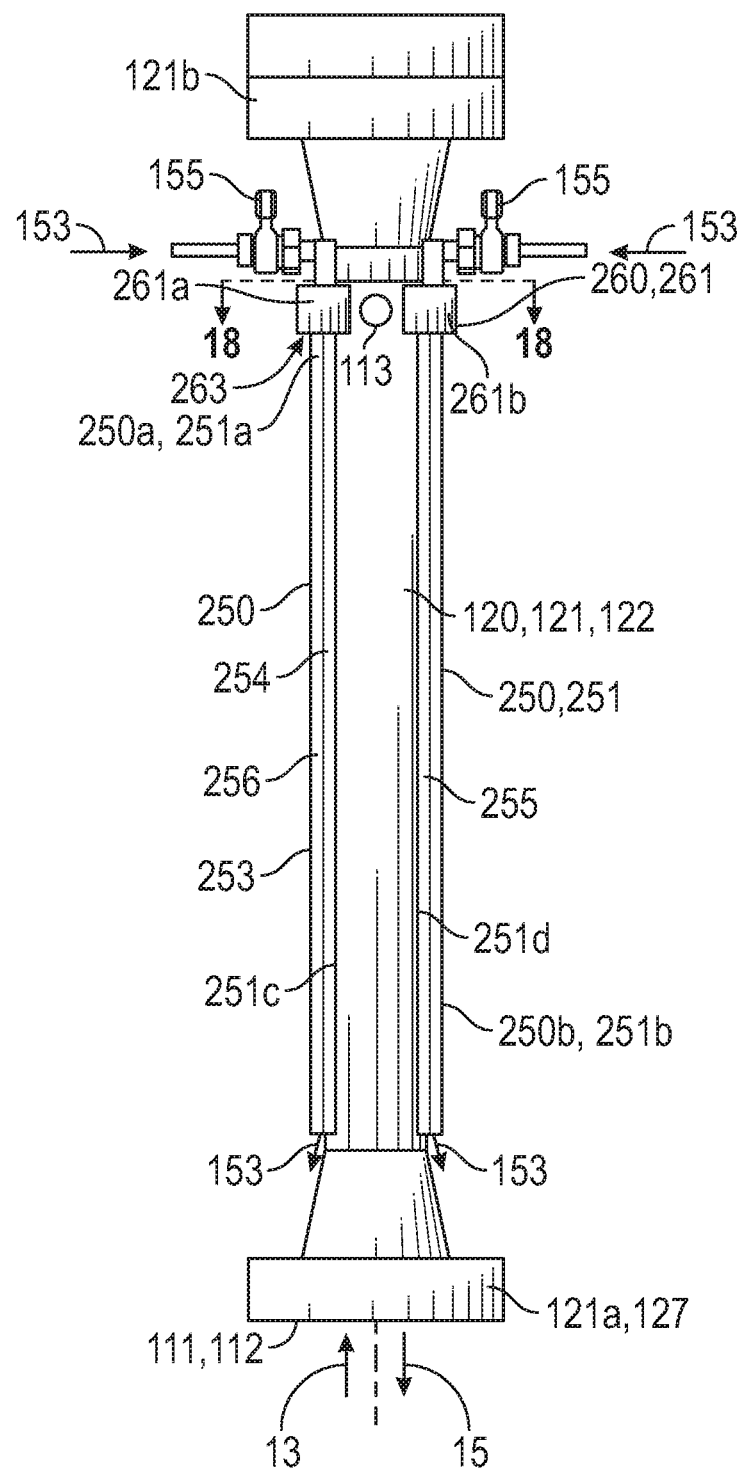
FIG. 17 is a side view of the fluid condition of FIG. 15 with the outer housing and the insulation removed.

Referring now to FIGS. 15-17, fluid separator 210 has a central or longitudinal axis 215, a first or lower end 210*a*, and a second or upper end 210*b*. As best shown in FIG. 16, moving radially outward from central axis 215, fluid separator 210 includes a separator assembly 120, a plurality of circumferentially-spaced tubular cooling conduits 250 disposed about separator assembly 120, insulation 280 disposed about separator assembly 120 and conduits 250, and a protective outer housing or tubular cover 270. Thus, conduits 250 and insulation 280 are radially positioned between separator assembly 120 and cover 270. Cover 270 provides a rigid shield that protects conduits 250, insulation 280, and separator assembly 120 from being impacted and damaged, as well as provides a secure base for mounting system 190 (i.e., system 190 is fixably secured to cover 270). Separator assembly 120 is as previously described. In FIG. 17, insulation 280 and protective cover 270 are not shown to more clearly illustrate separator assembly 120, cooling conduits 250, and the relationship therebetween. In this embodiment, separator 210 and its central axis 215 are vertically oriented, each being coaxially aligned with axis 125.

As best shown in FIG. 16, no annular gaps, spaces, or voids are provided between cover 270 and separator assembly 120. In particular, conduits 250 directly engage and contact separator assembly 120, and insulation 280 completely surrounds and encapsulates conduits 250 and assembly 120. Insulation 280 extends radially from cover 270 to conduits 250 and assembly 120, and in particular, insulation 280 directly engages cover 270, conduits 250, and the exposed portions of outer surface 122 circumferentially positioned between conduits 250. Thus, insulation 280 fills in the space circumferentially disposed between conduits 250 and fills in the space radially positioned between cover 270 and conduits 250.

Referring now to FIGS. 16 and 17, in this embodiment, cooling conduits 250 extend linearly (i.e., straight) along the outer surface 122 of conduit 121. In particular, the plurality of parallel cooling conduits 250 are vertically oriented and circumferentially-spaced apart about outer surface 122. Each cooling conduit 250 has a first or upper end 250*a* and a second or lower end 250*b* opposite end 250*a*. In this embodiment, each cooling conduit 250 comprises an elongate, thin strip or band 251 directly and fixably secured to outer surface 122 of conduit 121. More specifically, each band 251 has a first or upper end 251*a* defining end 250*a*, a second or lower end 251*b* defining end 250*b*, circumferentially-spaced lateral sides 251*c*, 251*d* extending axially between ends 251*a*, 251*b*, a first or inner surface 252 facing conduit 121, and a second or outer surface 253 facing away from conduit 121. The radial thickness of each band 251 measured between surfaces 252, 253 is uniform and constant along its axial length and circumferential width. As best shown in FIG. 16, each band 251 includes a pair of circumferentially-spaced, lateral attachment feet or sections 254, 255 and an intermediate arched or bulging C-shaped section 256 positioned between attachment sections 254, 255. Each section 254, 255 extends circumferentially from the corresponding side 251c, 251d, respectively, to intermediate section 256, and each section 254, 255 extends axially from upper end 251a to lower end 251b. Intermediate section 256 is circumferentially positioned between attachment sections 254, 255 and extends axially from upper end 251a to lower end 251b. Along attachment sections 254, 255, inner surface 252 is concave, and in particular, is disposed at a radius of curvature equal to the outer radius of conduit 121 (i.e., the radius of outer surface 122). Along intermediate section 256, inner surface 252 is also concave, but is disposed at a radius of curvature less than the outer radius of conduit 121.

Bands 251 are coupled to conduit 121 by directly securing attachment sections 254, 255 to outer surface 122 of conduit 121. Due to the matching of the radii of curvature of inner surface 252 along sections 254, 255 and outer surface 122, sections 254, 255 generally mate and conform to outer surface 122 of conduit 121. However, due to radius of curvature of inner surface 252 along intermediate section 256 being less than the radius of curvature of outer surface 122, intermediate section 256 bulges radially outward relative to conduit 121 and is radially spaced from outer surface 122. As a result, each cooling conduit 250 defines a flow passage 257 positioned between inner surface 252 along intermediate section 256 and the portion of outer surface 122 circumferentially disposed between attachment sections 254, 255.

In this embodiment, each band 251 is made of a durable, thermally conductive metal or metal alloy such as aluminum, stainless steel, or copper. In general, attachment sections 254, 255 can be directly secured to conduit 121 with any suitable means known in the art including, without limitation, an adhesive, welding, etc. In this embodiment, attachment sections 254, 255 are directly secured to conduit with a durable adhesive (e.g., heat paste) and a plurality of axially spaced annular hose clamps (not shown) are disposed about bands 251 to radially squeeze and compress attachment sections 254, 255 against outer surface 122.

In this embodiment, four cooling conduits 250 are provided, however, in other embodiments a different number of cooling conduits (e.g., conduits 250) may be provided. As best shown in FIG. 15-17, cooling conduits 250 are circumferentially positioned so as not to interfere with gas outlet 113. Consequently, in this embodiment, cooling conduits 250 are not uniformly circumferentially-spaced about conduit 121.

Figure 18:
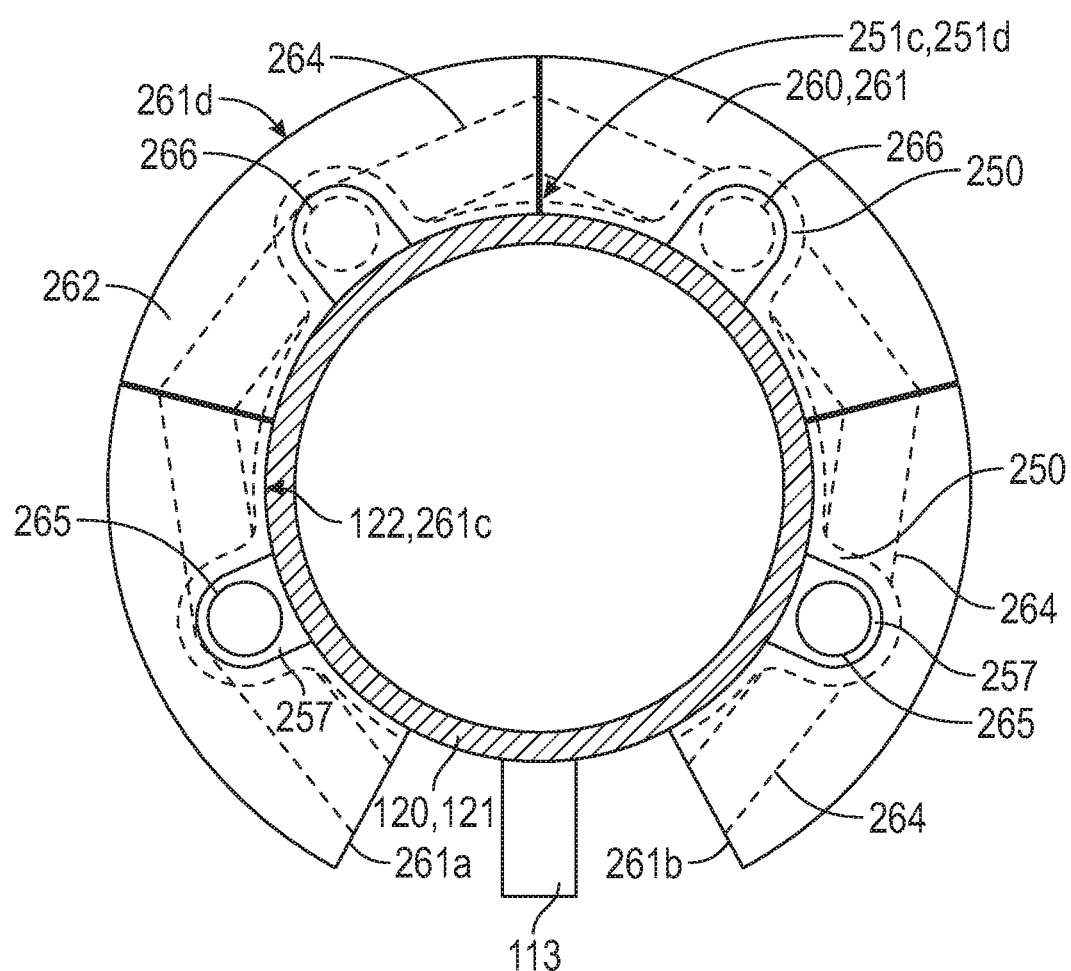
FIG. 18 is a cross-sectional top view fluid conditioner of FIG. 15 taken in section 18-18 of FIG. 17.

Referring now to FIGS. 17 and 18, a manifold 260 is disposed about conduit 121 proximal upper end 121b and coupled to upper ends 251a of cooling conduits 250. In this embodiment, manifold 260 has a generally C-shaped body 261 including circumferentially-spaced ends 261a, 261b, a radially inner surface 261c extending circumferentially between ends 261a, 261b, a radially outer surface 261d extending circumferentially between ends 261a, 261b, a first or upper planar surface 262 extending radially between surfaces 261c, 261d, and a second or lower planar surface 263 extending radially between surfaces 261c, 261d. In addition, manifold 260 includes an inner flow passage 264 extending generally circumferentially between ends 261a, 261b, a pair of inlet ports 265 extending axially (vertically) from upper surface 262 to flow passage 264, and a plurality of outlet ports 266 extending axially (vertically) from lower surface 263 to flow passage 264. Thus, ports 265, 266 and flow passages 264 are in fluid communication. Flow passage 264 is plugged or capped at each end 261a, 261b so as to prevent fluid communication between passage 264 and the surrounding environment. A cooling device 155 as previously described is coupled to each port 265 and supplies the cooling fluid or medium 153 to passage 264 via ports 265.

Upper ends 251a of cooling conduits 250 are directly attached to lower surface 263 of manifold 260 with each flow passage 257 circumferentially aligned with and in fluid communication with a corresponding port 266. Thus, ports 265, 266 and flow passages 264, 257 are in fluid communication. In this embodiment, upper ends 251a are welded to lower surface 263, thereby fixably and sealingly securing cooling conduits 250 to manifold 260.

Referring again to FIGS. 17 and 18, inner surface 261c of body 261 is a cylindrical surface disposed at the same or slightly larger radius as outer surface 122 of conduit 121, and thus, surfaces 261c, 122 mate and slidingly engage. In this embodiment, manifold 260 is positioned about conduit 121 with port 126 and associated gas outlet 113 circumferentially positioned between ends 261a, 261b. Thus, manifold 260 is axially (vertically) aligned with outlet 113. In general, manifold 260 can be secured to conduit 121 by any suitable means known in the art including, without limitation, adhesive, welding, etc. In this embodiment, manifold 260 comprises a plurality of circumferential segments positioned end-to-end that are radially squeezed and compressed against outer surface 122 with an annular hose clamp (not shown) that is disposed about manifold 260.

Referring now to FIG. 17, in this embodiment, cooling conduits 250 extend axially along substantially the entire length of conduit 121. In particular, upper ends 250a are positioned along conduit 121 proximal gas outlet 113 and lower ends 250b are positioned along conduit 121 proximal lower flange 127.

Similar to helical cooling coils 150 previously described, cooling conduits 250 are used to cool conduit 121 and the fluids therein (e.g., sample 13). In particular, the cooling fluid 153 flows from cooling devices 155 into ports 265 of manifold 260, which distributes the cooling fluid 153 to flow passages 257 of conduits 250. In particular, the cooling fluid or medium 153 enters manifold 260 via inlet ports 265, flows through flow passage 264 to outlet ports 266, and then flows through outlet ports 266 into passages 257 at upper ends 250a of cooling conduits 250. The cooling fluid 153 flows through passages 257 from upper end 250a to lower end 250b, where it exits conduits 250. Due to a temperature difference between the relatively hot sample 13 in conduit 121 and the relatively cold cooling fluid 153, thermal energy is transferred from the sample 13 through conduit 121 and/or conduits 250 to the cooling fluid 153, thereby reducing the temperature of sample 13 within conduit 121. To enhance the transfer of thermal energy between conduit 121 and cooling fluid 153, the contact surface area between conduits 250 and outer surface 122 of conduit 121 is enhanced via attachment sections 254, 255, and further, conduits 250 are made of a material having a relatively high thermal conductivity such as copper, aluminum, or stainless steel. Upon exiting conduits 250 at ends 250b, the cooling fluid 153 can be exhausted to the environment, or returned to the cooling device 155, re-cooled, and then recirculated back through conduits 250.

As previously described, cooling fluid 153 enters passages 257 at ends 250a and exits passages 257 at ends 250b. Accordingly, each flow passages 257 has an inlet at upper end 250a of the corresponding conduit 250 and an outlet at lower end 250b of the corresponding conduit 250. To enable a sufficient volumetric flow of cooling fluid 153, each flow passage 257 preferably has a diameter or width of 0.50 in. to 1.0 in.

Referring now to FIGS. 15 and 16, protective cover 270 is disposed about separator assembly 120, as well as manifold 260 and conduits 260 mounted to the outside of separator assembly 120. Cover 270 is an elongate tubular having a central or longitudinal axis 275, a first or upper end 270a, a second or lower end 270b, a cylindrical radially inner surface 271 extending axially between ends 270a, 270b, and a cylindrical radially outer surface 272 extending axially between ends 270a, 270b. Unlike cover 170 previously described, in this embodiment, cover 270 is made of a single cylindrical tubular sized to fit over assembly 120, manifold 260, and conduits 250 after manifold 260 and conduits 250 are mounted to assembly 120. In other words, in this embodiment, cover 270 is not made of two semi-cylindrical halves that are attached together.

Cover 270 protects the components disposed therein (e.g., manifold 260, conduits 250, insulation 280, etc.) from inadvertently being damaged (e.g., shields these components from impact loads). Accordingly, cover 270 is preferably made of a durable rigid material such as steel, stainless steel, copper, or aluminum. Cover 270 also provides a base to which sample monitoring and control system 190 can be securely coupled. In this embodiment, a pair of axially spaced mounts or connectors 176 extend radially from cover 270. Connectors 176 provide a means for securing sample monitoring and control system 190 to separator 210.

Insulation 280 fills the annular space between cover 270 and manifold 260, conduits 250, and assembly 120. In addition, insulation 280 insulates the components disposed therein. In general, insulation 280 functions to limit the transfer of thermal energy between conduits 121, 250 and the surrounding environment to facilitate the transfer of thermal energy between sample 13 in conduit 121 and cooling fluid 153 in conduits 250. In general, insulation 280 can be any suitable insulation known in the art. In this embodiment, insulation 280 is an closed cell foam that is (i) injected into the annulus between cover 270 and manifold 260, conduits 250, and assembly 120 after positioning cover about manifold 260, conduits 250, and assembly 120, and (ii) allowed to expand, cure, and dry to completely fill the annulus and encapsulate manifold 260, conduits 250, and the portion of assembly 120 disposed within cover 270.

In general, system 10' and associated fluid condition 200 function in the same manner as system 10 and fluid conditioner 100 previously described. Namely, during sampling operations, cooling devices 155 are turned on with actuators 158, and valves 191 of cooling devices 155 are maintained in the opened position with the corresponding actuators 192. As a result, cooling fluid 153 flows through valves 191 to cooling devices 155, which reduces the temperature of the cooling fluid 153 exiting each cooling device 155. In this embodiment, the cooling fluid 153 supplied by each cooling device 155 is chilled air. The temperature of cooling fluid 153 at the inlet of each conduit 250 is preferably 0° F. to 50° F., and more preferably 38° F. to 42° F. The temperature of cooling fluid 153 at the inlet of each conduit 250 is indirectly measured with inlet temperature sensors 149 associated with cooling device 155, which measure the temperature of cooling fluid 153 at each inlet 265 of manifold 260. Based on the temperature of cooling fluid 153 at each inlet 265, cooling devices 155 are controlled via actuators 158 to maintain, increase, or decrease the temperature of cooling fluid 153 to achieve the desired temperature for cooling fluid 153 at inlets 265.

Cooling fluid 153 is cooled by cooling devices 155 and flows through manifold 260 and conduits 260 as previously described. As cooling fluid 153 flows through conduits 250, it cools conduits 250 and conduit 121. Conduits 250 directly contact conduit 121, and thus, also cool conduit 121. Simultaneously, unconditioned fluid sample 13 is pulled from bulk fluid stream 12 and enters inlet 111 at the lower end 121a of conduit 121 and flows therethrough. Thus, conduit 121 is in direct contact with the relatively cold conduits 150 and cooling fluid 153 flowing through passages 257, and in direct contact with the relatively hot fluid sample 13. As a result, conductive heat transfer occurs between conduit 121 and conduits 250. In particular, thermal energy in fluid sample 13 is transferred across conduit 121 and conduits 250 into cooling fluid 153, thereby increasing the temperature of cooling fluid 153 as it moves through conduits 250 and decreasing the temperature of fluid sample 13 as it migrates upwardly through conduit 121. Thus, separator 210 transfers thermal energy from fluid sample 13 into cooling fluid 153.

The unconditioned fluid sample 13 enters inlet 111 at the lower ends 110a, 121a and migrates upward through conduit 121 in the same manner as previously described. The decreasing temperature and increasing pressure of fluid sample 13 as it migrates upward within conduit 121 brings the molecules in unconditioned fluid sample 13 closer together and facilitate the coalescence of contaminants 15 (i.e., water and heavy hydrocarbons), which form relatively heavy liquid droplets that drain and flow under the force of gravity downward to lower end 121a, and then exit conduit 121 via contaminant outlet 112 back into the bulk fluid stream 12. The remaining unconditioned fluid sample 13, which has been at least partially conditioned by the removal of some contaminants 15, continues to migrate upward through fluid orifices 135 to outlet 113. Thus, the unconditioned fluid sample 13 is gradually transformed into conditioned gas 14 by the gradual separation and removal of contaminants 15. Contaminants 15 are continuously separated and removed from unconditioned fluid sample 13 as it migrates through separator assembly 120.

During sampling operations with fluid conditioner 200, system 190 acquires real-time information relating to (a) the temperature of cooling fluid 153 at inlets 265 of manifold 260 and the outlet of each conduit 260; (b) the temperature of conditioned gas 14 at upper end 121b; (c) the status and position of each valve 191, 193 (e.g., open, closed, etc.); and (d) the status of each cooling device 155 (e.g., on, off, etc.). In addition, by controlling valves 191 and cooling devices 155 with actuators 192, 158, respectively, system 190 is capable of controlling the temperature of cooling fluid 153 at inlets 265, which in turn allows system 190 to control the temperature of cooling fluid 153 within conduits 250 and the outlets of each conduit 250, as well as control the temperature of fluid sample 13. Still further, by controlling valve 193 with actuator 194, system 190 is capable of controlling the flow of conditioned gas 14 flowing from separator 210 to analytical instrumentation 30.

The temperature of cooling fluid 153 at each inlet 265 of manifold 260 is preferably maintained at 0° F. to 50° F., and more preferably 38° F. to 42° F. This temperature range for cooling fluid 153 results in sufficient heat transfer from unconditioned fluid sample 13 to achieve an acceptable temperature for unconditioned fluid sample 13 (i.e., a temperature sufficiently low to achieve the desired separation and removal of contaminants 15). In particular, a cooling fluid inlet temperature of 0° F. to 50° F., and more preferably 38° F. to 42° F. results in a conditioned gas 14 outlet temperature of 40° F. to 65° F. If the temperature of cooling fluid 153 at inlets 265, as indirectly measured by temperature sensors 149, is too low, the degree of cooling provided by cooling devices 155 may be decreased via actuators 158.

On the other hand, if the temperature of cooling fluid 153 at inlets 265, as indirectly measured by temperature sensors 149, is too high, the degree of cooling provided by cooling devices 155 may be increased via actuators 158. In some instances, the temperature of unconditioned fluid sample 13 and conditioned gas 14 may still be too high. For example, the temperature of the bulk fluid stream 12 may unexpectedly spike, all cooling devices 155 may be operating at maximum capacity but still cannot achieve the preferred temperature for cooling fluid 153 at inlet 265. If the temperature of conditioned gas 14 at upper end 121b, as measured by upper temperature sensor 148, is sufficiently high, such that an insufficient quantity of contaminants 15 were separated and removed, then system 190 can actuate valve 193 to the closed position with actuator 194, thereby restricting and/or preventing conditioned gas 14 from flowing to analytical instrumentation 30.

Embodiments described herein offer the potential for several improvements over existing sampling and conditioning devices. For example, embodiments of fluid conditioners described herein (e.g., fluid conditioners 100, 200) that employ a closed loop cooling system (e.g., recirculated cooling medium 153) can be operated with a variety of different cooling fluids 153 including, without limitation, air, water, gas, and Freon. As another example, embodiments of flexible baffle assemblies (e.g., baffle assembly 130) described herein can be used in applications where there is limited overhead clearance. Still further, embodiments of fluid conditioners described herein offer the potential for improved cooling efficiency as compared to some conventional fluid conditioners of similar size and capacity. In particular, embodiments described herein allow for sample flow rates up to about 12 liters per minute with about 30% less cooling fluid volumetric flow rate (30 CFM of cooled air as compared to 40 CFM of cooled air for the same sample flow rate).

Although some embodiments shown and described herein are discussed in context of conditioning a decoke fluid sample from a hydrocarbon cracking operation to determine ethylene and/or propylene yields, in general, embodiments described herein may be used to condition other fluid samples In particular, embodiments of conditioner 100 may be used where high moisture content, heavy hydrocarbons, particulate matter, and/or combinations thereof may be present in the unconditioned fluid sample and need to be removed prior to analysis. For example, embodiments described herein may be used to remove "green oil" from recycle gas or on a furnace decoke header to remove water and heavy particulates.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A distillation probe, comprising:
   a conduit having a central axis;
   a baffle assembly disposed in the conduit, wherein the baffle assembly includes a plurality of axially-spaced baffles positioned one-above-the-other in a stack within the conduit;
   a first helical cooling coil wrapped around the conduit and contacting the conduit;
   a thermally conductive layer disposed about the conduit and the first helical cooling coil, wherein the thermally conductive layer encapsulates the first helical cooling coil and is configured to transfer thermal energy between the first helical cooling coil and the conduit; and
   a plurality of flexible cables extending axially through each of the baffles of the baffle assembly, wherein each flexible cable is radially spaced from the central axis.

2. The distillation probe of claim 1, wherein the first helical coil is positioned radially adjacent the conduit.

3. The distillation probe of claim 2, further comprising:
   insulation disposed about the thermally conductive layer; and
   a protective cover positioned between the insulation and the thermally conductive layer.

4. The distillation probe of claim 1, further comprising a second helical cooling coil wrapped around the conduit, wherein the first helical cooling coil and the second helical cooling coil are intermeshed.

5. The distillation probe of claim 4, wherein the first helical coil and the second helical coil are radially adjacent the conduit.

6. The distillation probe of claim 1, wherein each baffle includes a plurality of cable holes extending axially therethrough and at least one fluid orifice extending axially therethrough, wherein each flexible cable extends through one of the plurality of cable holes of each baffle.

7. The distillation probe of claim 6, wherein each baffle includes a plurality of fluid orifices, and wherein the fluid orifices in each pair of axially adjacent baffles are out of alignment.

8. The distillation probe of claim 7, wherein each fluid orifice has a diameter between ⅛ in and ½ in.

9. The distillation probe of claim 1, wherein each baffle is a flat disc having an upper planar surface, a lower planar surface, and an outer cylindrical surface extending axially between the upper planar surface and the lower planar surface;
   wherein the outer cylindrical surface of each baffle slidingly engages an inner cylindrical surface of the conduit.

10. The distillation probe of claim 1, wherein the conduit has an upper end and a lower end;
    wherein the first helical cooling coil has an inlet proximal the upper end and an outlet proximal the lower end;
    wherein the conduit includes an inlet at the lower end, an outlet at the lower end, and an outlet proximal the upper end.

11. The distillation probe of claim 1, wherein an upper end of each flexible cable comprises a loop configured to enable installation of the baffle assembly into the conduit and removal of the baffle assembly from the conduit.

12. A fluid sampling system, comprising:
a fluid separator assembly including a conduit and a baffle assembly disposed in the conduit, wherein the conduit has a central axis, wherein the baffle assembly includes:
 a plurality of axially-spaced baffles positioned one-above-the-other in a stack within the conduit, wherein each baffle includes a cable hole extending axially therethrough; and
 a flexible cable extending through the cable hole in each baffle and configured to allow insertion of the plurality of baffles together into the conduit and removal of the plurality of baffles together from the conduit;
a plurality of cooling conduits mounted to the conduit and positioned radially adjacent the conduit, wherein the cooling conduits are configured to cool the fluid separator assembly;
wherein the plurality of cooling conduits are circumferentially-spaced and extend axially along the conduit of the fluid separator;
wherein each cooling conduit comprises an elongate strip having an upper end, a lower end, a radially inner surface directly attached to the conduit, and a radially outer surface distal the conduit;
wherein each elongate strip has a first lateral side extending axially from the upper end to the lower end, a second lateral side extending axially from the upper end to the lower end, a first attachment section extending circumferentially from the first lateral side, a second attachment section extending circumferentially from the second lateral side, and an intermediate section circumferentially positioned between the first attachment section and the second attachment section;
wherein the first attachment section and the second attachment section of each elongate strip is directly attached to the conduit and the intermediate section of each elongate strip is radially spaced from the conduit.

13. The system of claim 12, wherein each baffle includes at least one fluid orifice extending therethrough.

14. The system of claim 13, wherein each baffle includes a plurality of fluid orifices, and wherein the fluid orifices in each pair of axially adjacent baffles are out of alignment.

15. The system of claim 13, wherein the fluid orifice of each baffle is disposed at a different angular orientation about the central axis than the fluid orifice of each axially adjacent baffle.

16. The system of claim 13, wherein each fluid orifice has a diameter between ⅛ in and ½ in.

17. The system of claim 12, wherein each baffle is a flat disc having an upper planar surface, a lower planar surface, and an outer cylindrical surface extending axially between the upper planar surface and the lower planar surface.

18. The system of claim 17, wherein the outer cylindrical surface of each baffle slidingly engages an inner cylindrical surface of the conduit.

19. The system of claim 12, wherein the cable hole is radially spaced from the central axis.

20. The system of claim 12, wherein the fluid separator assembly has an upper end and a lower end;
wherein each cooling conduit has an inlet proximal the upper end and an outlet proximal the lower end;
wherein the conduit of the separator assembly includes an inlet at the lower end, an outlet at the lower end, and an outlet proximal the upper end.

21. The system of claim 20, further comprising a cooling device configured to cool a fluid, wherein the cooling device is in fluid communication with the inlet of at least one of the cooling conduits.

22. The system of claim 20, further comprising:
a monitoring and control system coupled to the fluid separator assembly, the monitoring and control system comprising:
 a first temperature sensor coupled to an upper end of the fluid separator assembly and configured to measure the temperature within the conduit of fluid separator assembly proximal the upper end;
 a second temperature sensor coupled to a lower end of the fluid separator assembly and configured to measure the temperature within the conduit of fluid separator assembly proximal the lower end;
 a third temperature sensor coupled to one of the cooling conduits and configured to measure the temperature at the inlet of the cooling conduit.

23. The system of claim 12, further comprising a manifold at least partially disposed about the conduit of the fluid separator and configured to distribute a cooling fluid to the plurality of cooling conduits.

24. The system of claim 23, wherein the upper end of each cooling conduit is coupled to the manifold, and the lower end of each cooling conduit is distal the manifold.

25. The system of claim 12, further comprising a plurality of flexible cables extending axially through each of the baffles of the baffle assembly, wherein each flexible cable is radially spaced from the central axis.

26. The distillation probe of claim 25, wherein an upper end of each flexible cable comprises a loop configured to enable installation of the baffle assembly into the conduit and removal of the baffle assembly from the conduit.

* * * * *